US010617452B2

(12) United States Patent
Jackson

(10) Patent No.: US 10,617,452 B2
(45) Date of Patent: Apr. 14, 2020

(54) SPINAL FIXATION TOOL SET AND METHOD

(71) Applicant: Roger P. Jackson, Prairie Village, KS (US)

(72) Inventor: Roger P. Jackson, Prairie Village, KS (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 15/972,454

(22) Filed: May 7, 2018

(65) Prior Publication Data
US 2018/0250039 A1 Sep. 6, 2018

Related U.S. Application Data

(63) Continuation of application No. 14/968,623, filed on Dec. 14, 2015, now Pat. No. 9,987,054, which is a (Continued)

(51) Int. Cl.
A61B 17/70 (2006.01)

(52) U.S. Cl.
CPC ...... A61B 17/7086 (2013.01); A61B 17/7037 (2013.01); A61B 17/7082 (2013.01); (Continued)

(58) Field of Classification Search
CPC ............ A61B 17/7074; A61B 17/7076; A61B 17/7082; A61B 17/7083; A61B 17/7091; (Continued)

(56) References Cited

U.S. PATENT DOCUMENTS 5,257,993 A   11/1993 Asher et al.
5,545,165 A    8/1996 Biedermann et al.
(Continued)

OTHER PUBLICATIONS

International Search Report and Written Opinion PCT/US2015/056706, dated Jan. 6, 2016.
(Continued)

Primary Examiner — Julianna N Harvey
Assistant Examiner — Christina Negrellirodriguez

(57) ABSTRACT

A tool set for implanting a rod in a human spine in conjunction with bone screws includes a pair of end guide tools that receive opposite ends of the rod in channels and under manipulation by a surgeon facilitate transport of the rod toward the bone screws attached to the guide tools. Each end guide tool includes a laterally extending, rigid, rod holding structure located near a bottom surface thereof. Intermediate guide tools having pass-through slots are utilized to guide the rod to the bone screws at intermediate locations. For bone screw implantation, the end guide tools and intermediate guide tools are assembled with a driver. The driver is coaxial with the respective guide tool and rotatingly mateable thereto. The driver includes a stem and a nut-type fastener, the stem receivable in the guide tool. The fastener allows for rotation of the bone screw without rotating the attached guide tool. For reducing a rod into the bone screw, a rod pusher is deployed that is coaxial with a respective guide tool and includes an outer sleeve that abuts the rod as the sleeve is translated along the guide tool and toward the bone screw. A method utilizing the tool set allows a surgeon to percutaneously implant the bone screws and the rod in the patient.

20 Claims, 17 Drawing Sheets

Related U.S. Application Data continuation of application No. 12/924,223, filed on Sep. 23, 2010, now Pat. No. 9,211,150, which is a continuation of application No. 10/996,289, filed on Nov. 23, 2004, now Pat. No. 8,152,810.

(52) U.S. Cl.
CPC ...... *A61B 17/7085* (2013.01); *A61B 17/7088* (2013.01); *A61B 17/7091* (2013.01); *A61B 17/7011* (2013.01); *A61B 17/7032* (2013.01); *Y10T 29/49826* (2015.01)

(58) Field of Classification Search
CPC ............ A61B 17/7001; A61B 17/7032; A61B 17/7034
USPC .......................... 606/264–278, 86 A, 99, 104
See application file for complete search history.

(56) References Cited

U.S. PATENT DOCUMENTS

| | | | |
|---|---|---|---|
| 5,716,356 A | 2/1998 | Biedermann et al. | |
| 5,720,751 A | 2/1998 | Jackson | |
| 5,873,878 A | 2/1999 | Harms et al. | |
| 5,910,141 A | 6/1999 | Morrison et al. | |
| 6,077,262 A | 6/2000 | Schlapfer et al. | |
| 6,139,549 A * | 10/2000 | Keller | A61B 17/7032 606/104 |
| 6,273,888 B1 | 8/2001 | Justis | |
| 6,287,311 B1 | 9/2001 | Sherman et al. | |
| 6,302,888 B1 | 10/2001 | Mellinger et al. | |
| 6,440,133 B1 | 8/2002 | Beale et al. | |
| 6,540,749 B2 | 4/2003 | Schafer et al. | |
| 6,565,565 B1 | 5/2003 | Yuan et al. | |
| 6,648,888 B1 | 11/2003 | Shluzas | |
| 6,660,006 B2 | 12/2003 | Markworth et al. | |
| 6,905,500 B2 | 6/2005 | Jeon et al. | |
| 7,066,937 B2 | 6/2006 | Shluzas | |
| 7,087,057 B2 | 8/2006 | Konieczynski et al. | |
| 7,144,396 B2 | 12/2006 | Shluzas | |
| 7,179,261 B2 * | 2/2007 | Sicvol | A61B 17/7032 606/86 A |
| 7,250,052 B2 | 7/2007 | Landry et al. | |
| 7,377,923 B2 | 5/2008 | Purcell et al. | |
| 7,476,228 B2 | 1/2009 | Abdou | |
| 7,476,239 B2 | 1/2009 | Jackson | |
| 7,559,943 B2 | 7/2009 | Mujwid | |
| 7,618,440 B2 | 11/2009 | Gray et al. | |
| 7,618,444 B2 | 11/2009 | Shluzas | |
| 7,625,396 B2 | 12/2009 | Jackson | |
| 7,641,670 B2 | 1/2010 | Davison et al. | |
| 7,686,835 B2 | 3/2010 | Warnick | |
| 7,736,305 B2 | 6/2010 | DiPoto | |
| 7,776,040 B2 | 8/2010 | Markworth et al. | |
| 7,815,650 B2 | 10/2010 | Shluzas et al. | |
| 7,862,587 B2 | 1/2011 | Jackson | |
| 7,875,065 B2 | 1/2011 | Jackson | |
| 7,887,539 B2 | 2/2011 | Dunbar et al. | |
| 8,273,089 B2 | 9/2012 | Jackson | |
| 8,308,782 B2 | 11/2012 | Jackson | |
| 8,709,051 B2 | 4/2014 | Hammer et al. | |
| 9,522,021 B2 | 12/2016 | Jackson | |
| 9,629,669 B2 | 4/2017 | Jackson | |
| 9,700,354 B2 | 7/2017 | Jackson | |
| 2002/0161368 A1 | 10/2002 | Foley et al. | |
| 2003/0158552 A1 | 8/2003 | Jeon | |
| 2005/0065517 A1 | 3/2005 | Chin | |
| 2005/0192589 A1 | 9/2005 | Raymond et al. | |
| 2005/0277928 A1 | 12/2005 | Boschert | |
| 2008/0077139 A1 | 3/2008 | Landry et al. | |
| 2014/0031873 A1 | 1/2014 | Jackson | |
| 2016/0302835 A1 | 10/2016 | Jackson | |
| 2017/0265902 A1 | 9/2017 | Jackson | |

OTHER PUBLICATIONS

International Preliminary Report on Patentability regarding PCT/US2015/056706, dated Nov. 17, 2016.

* cited by examiner

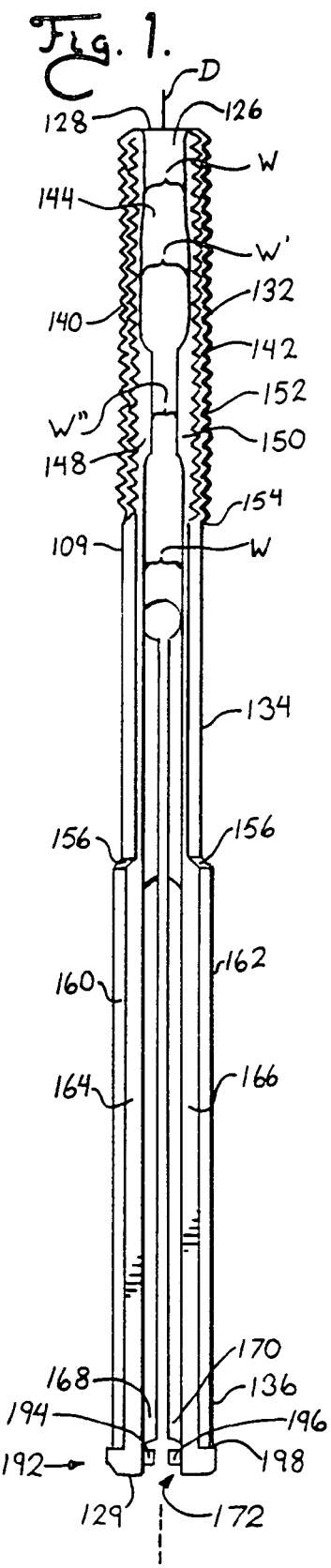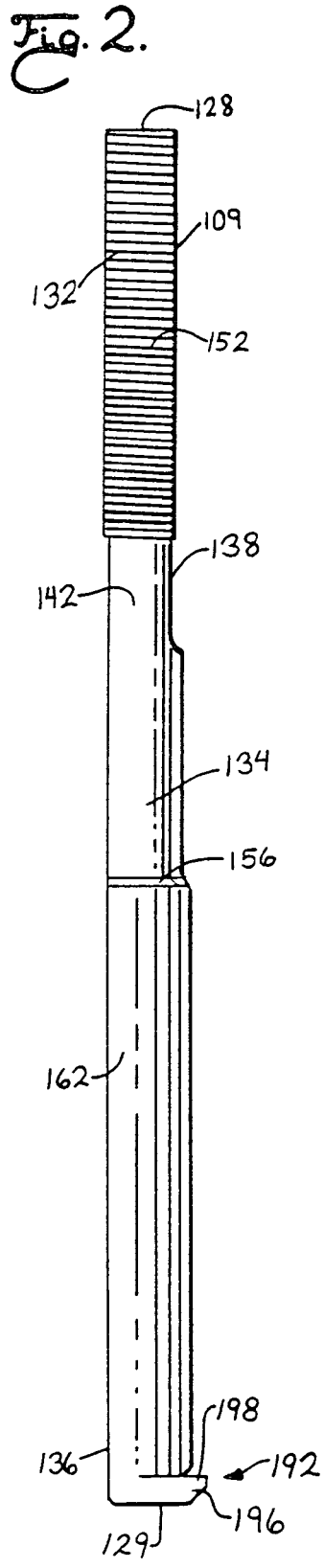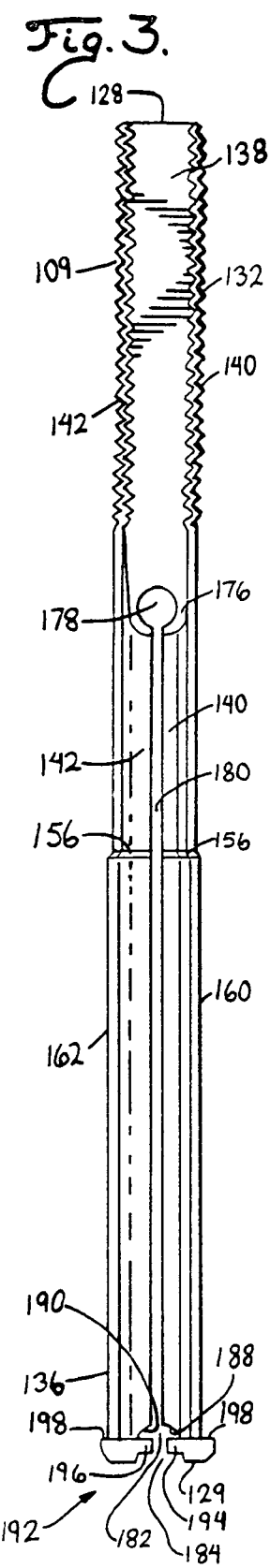

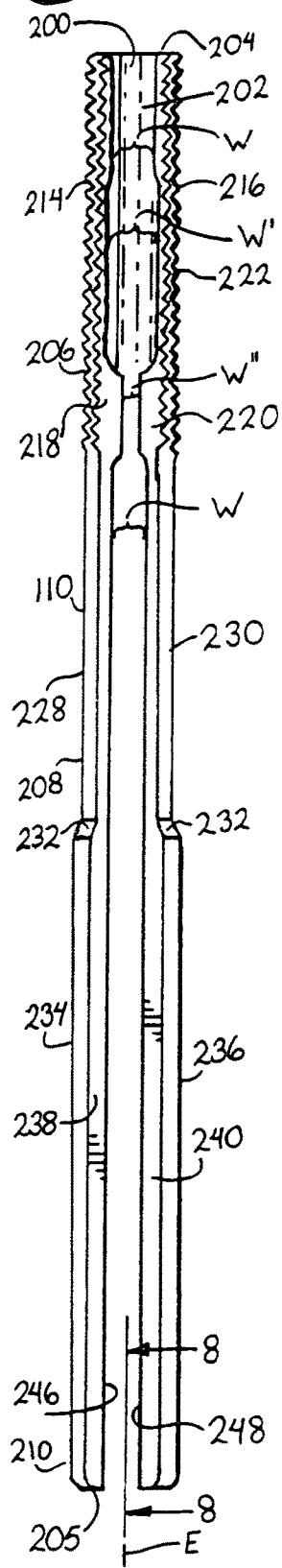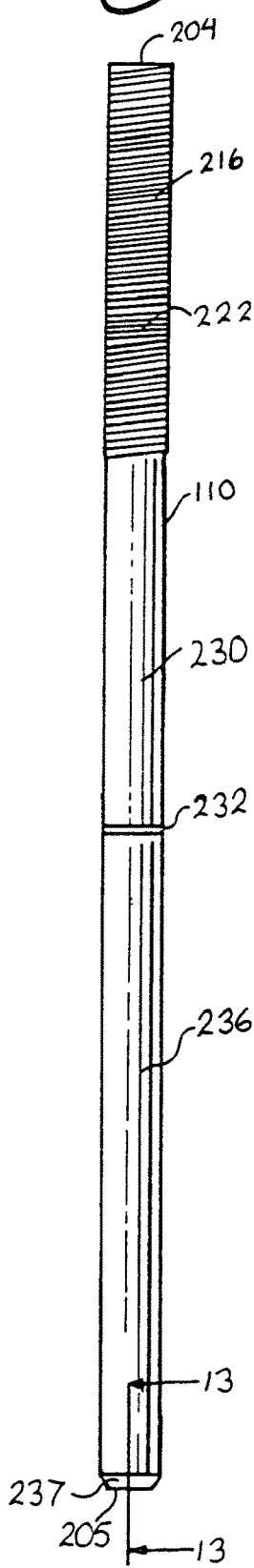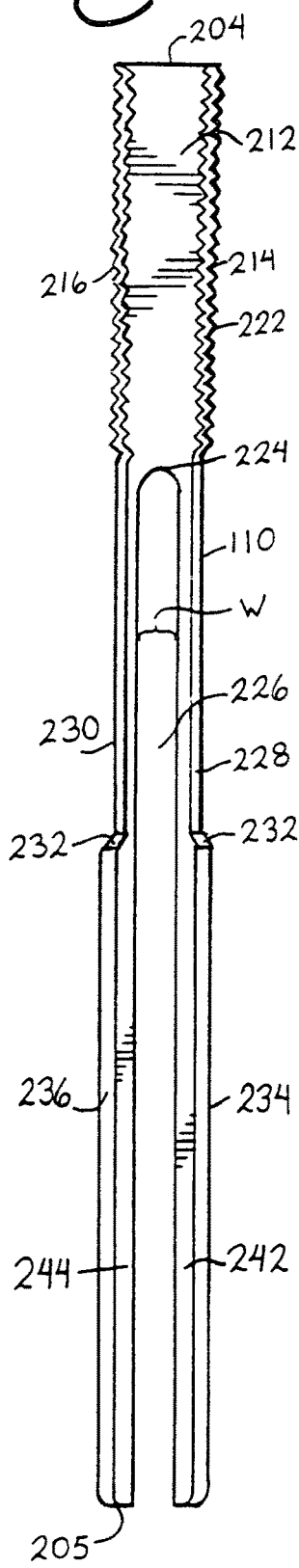

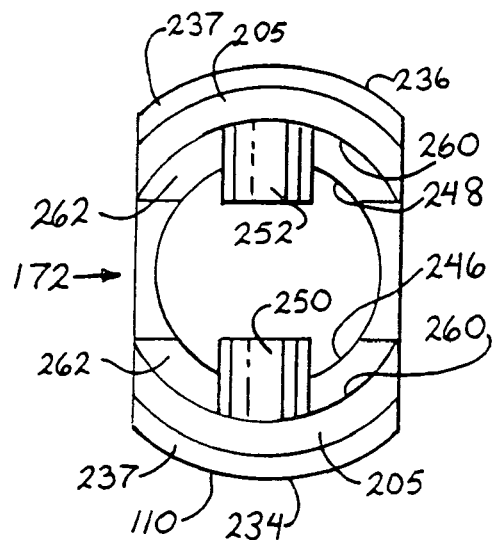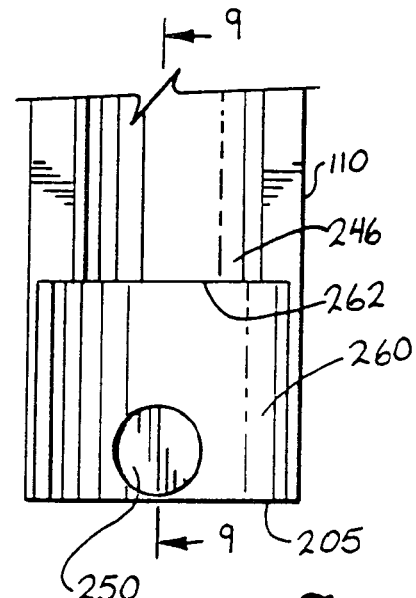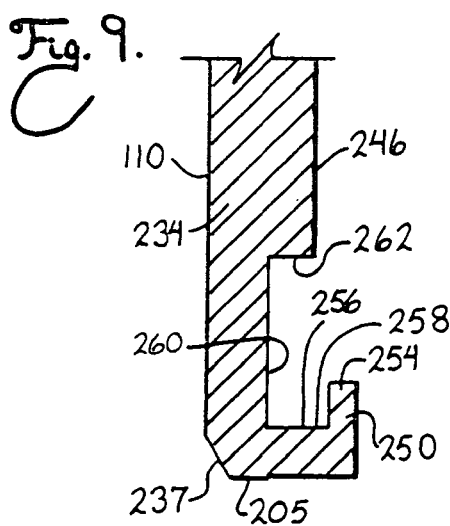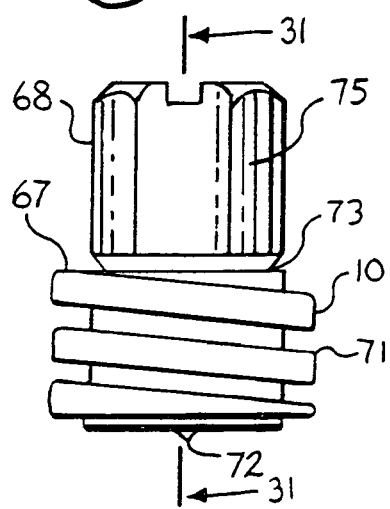

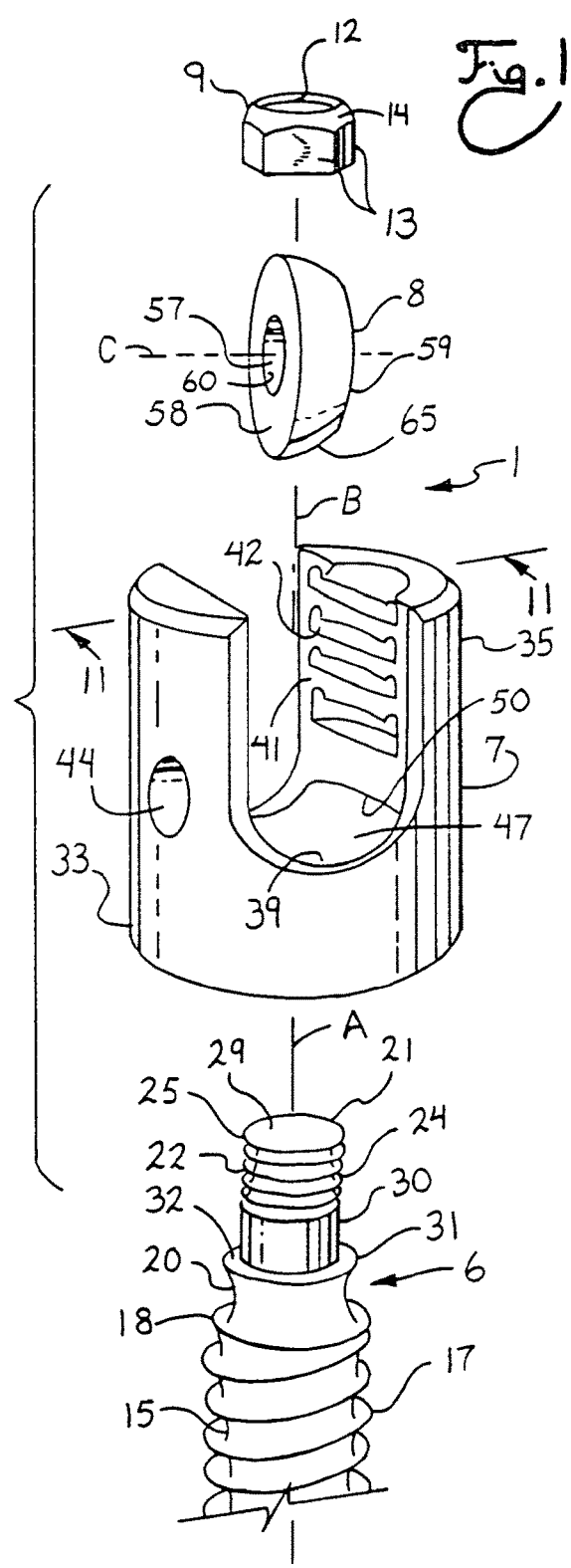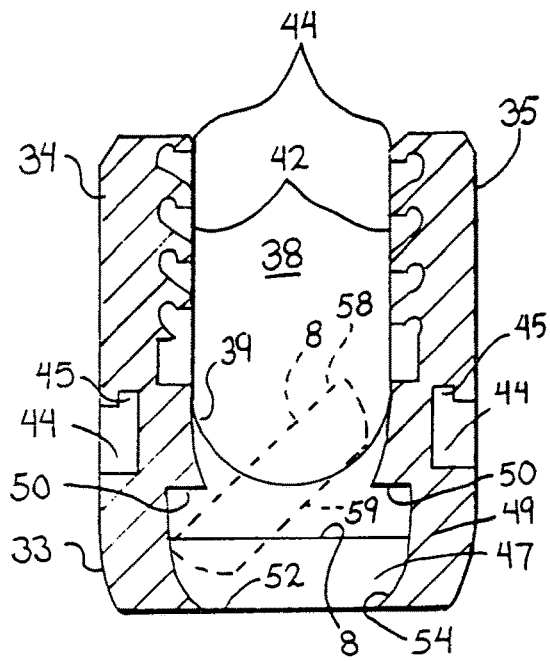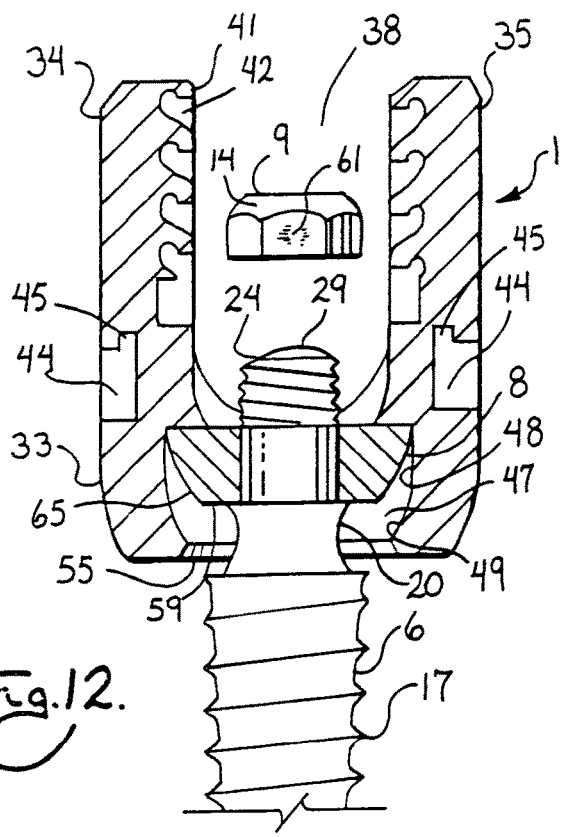

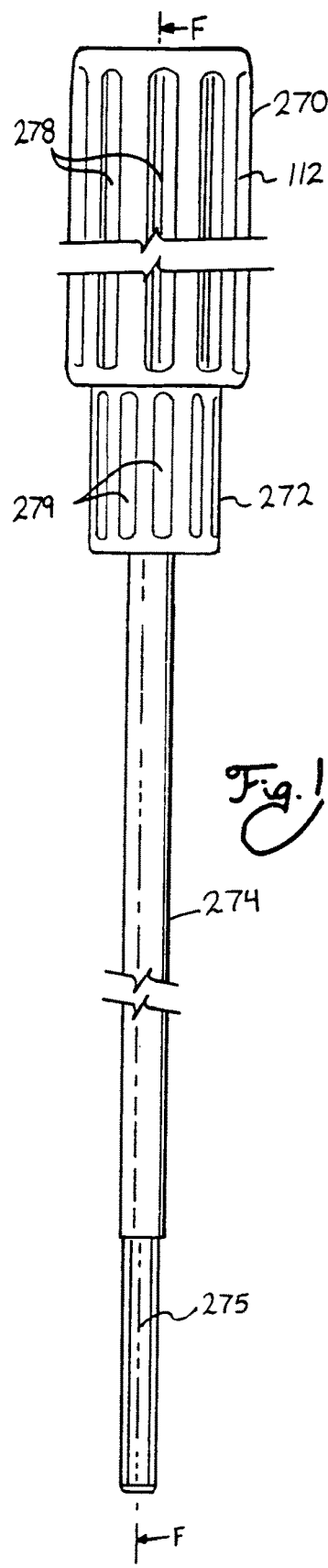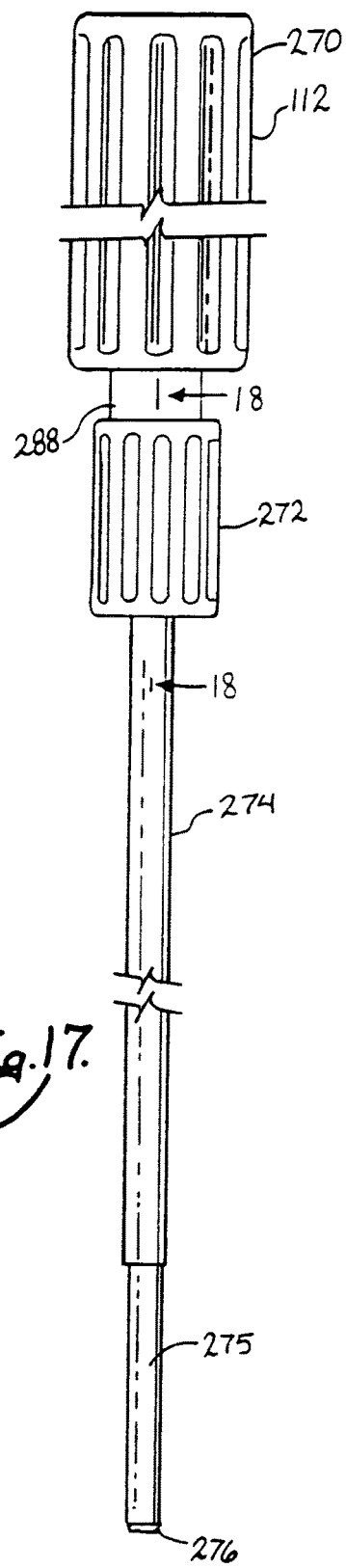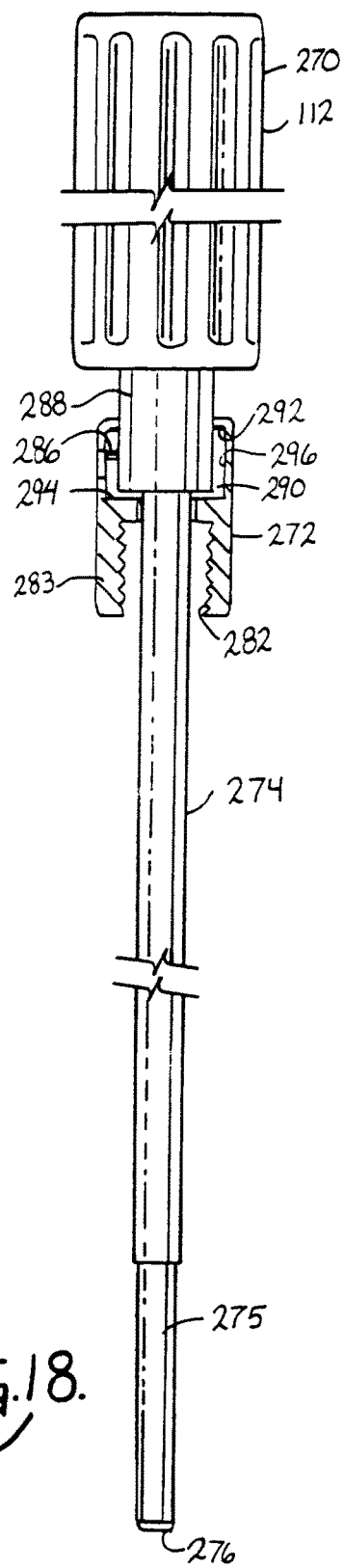

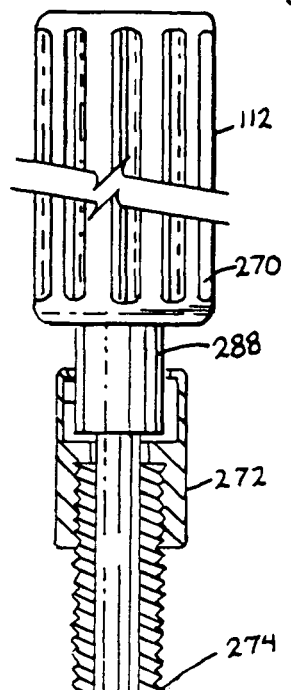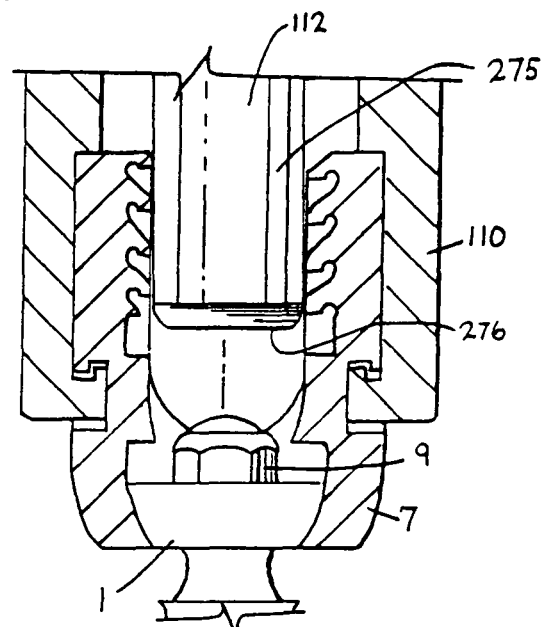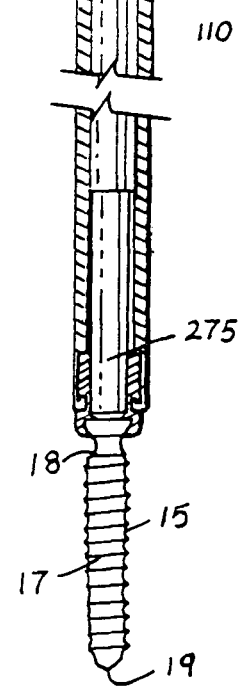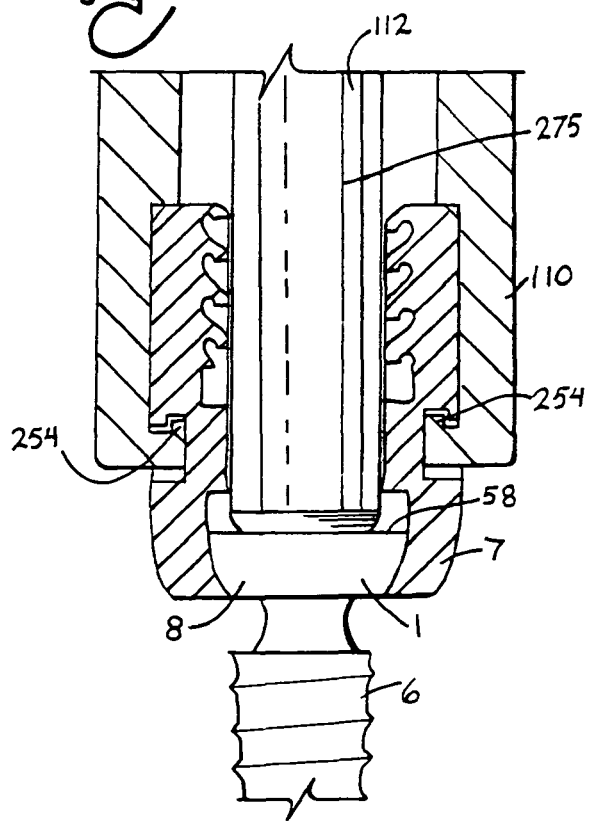
Fig. 19.
Fig. 20.
Fig. 21.

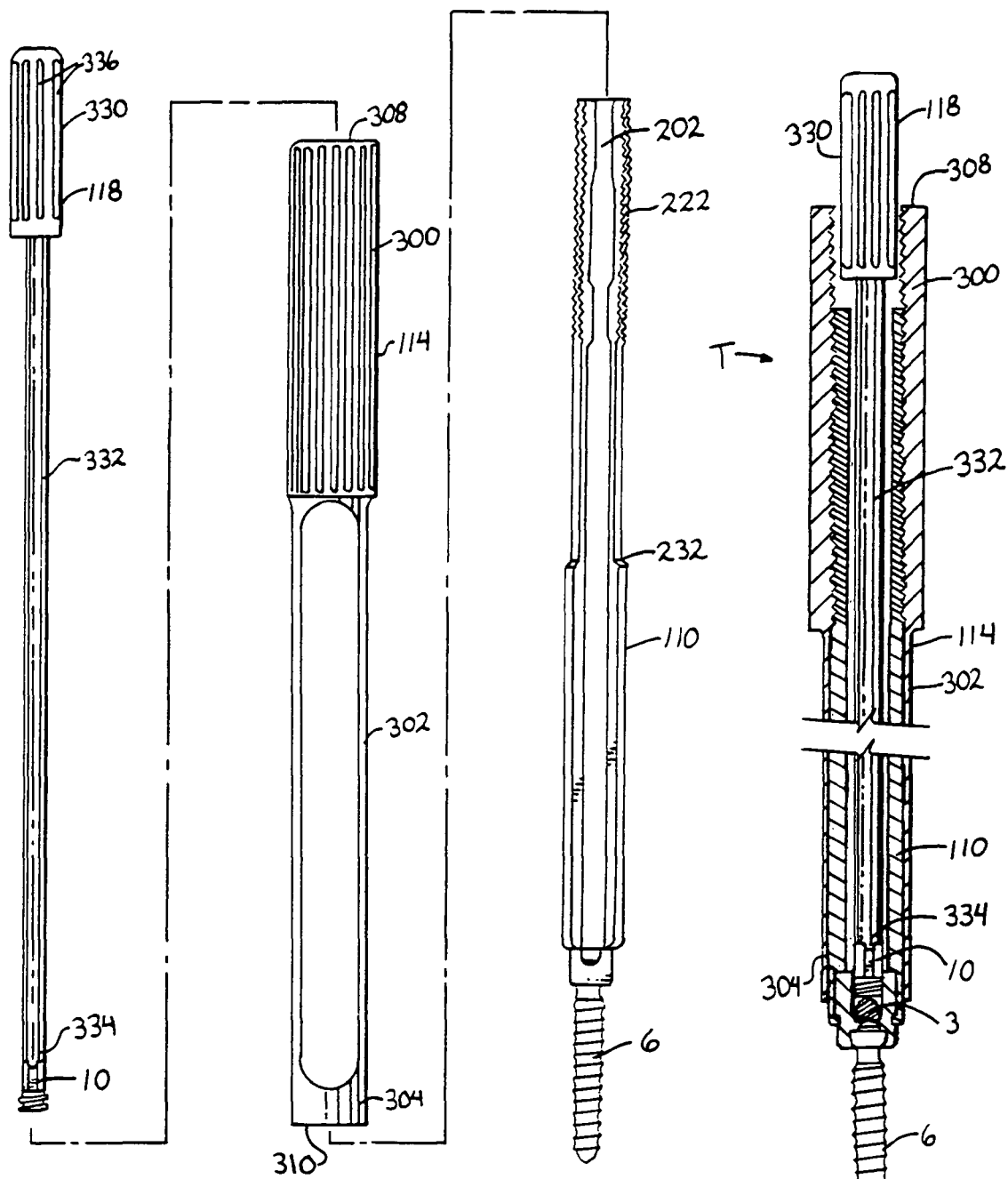

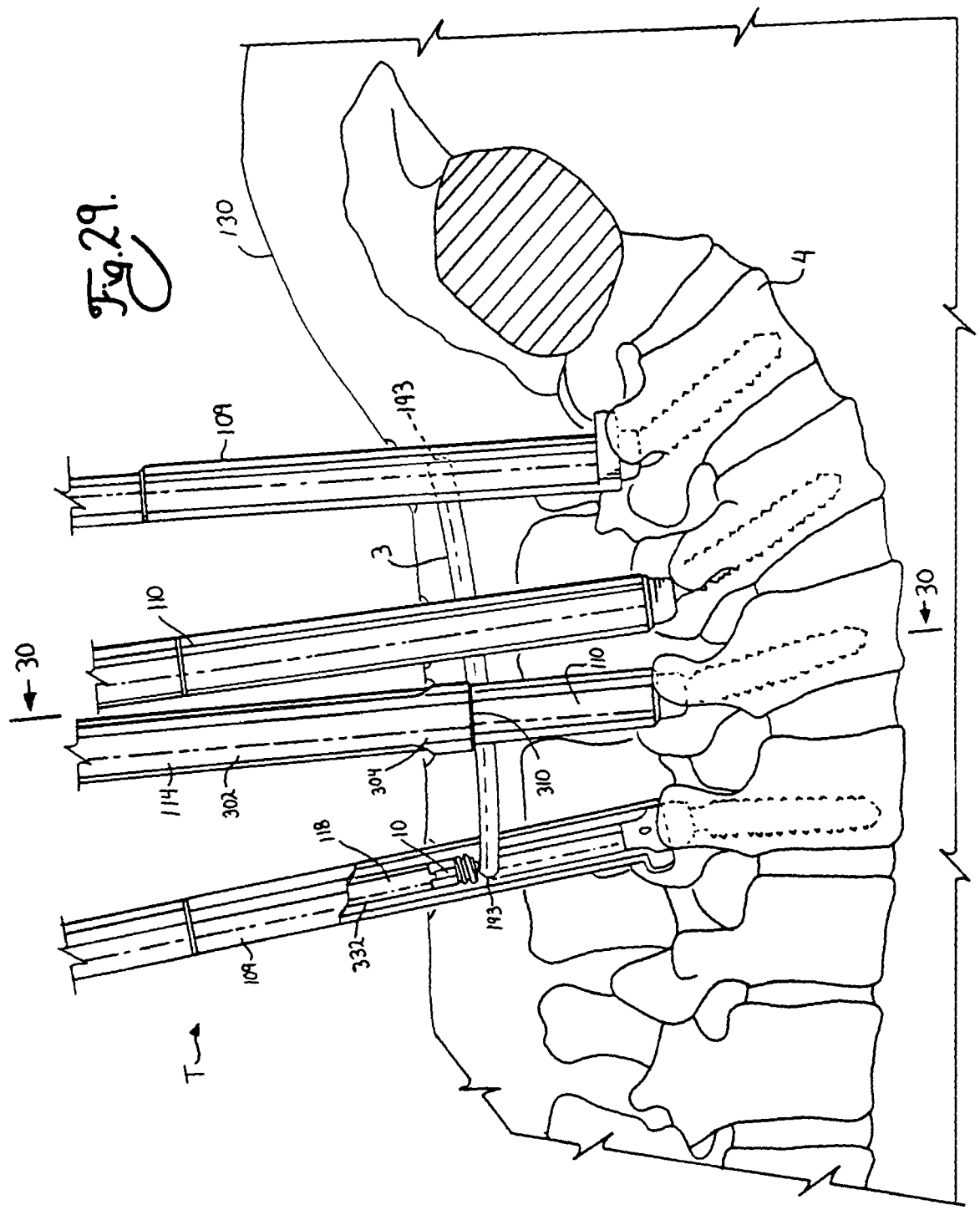

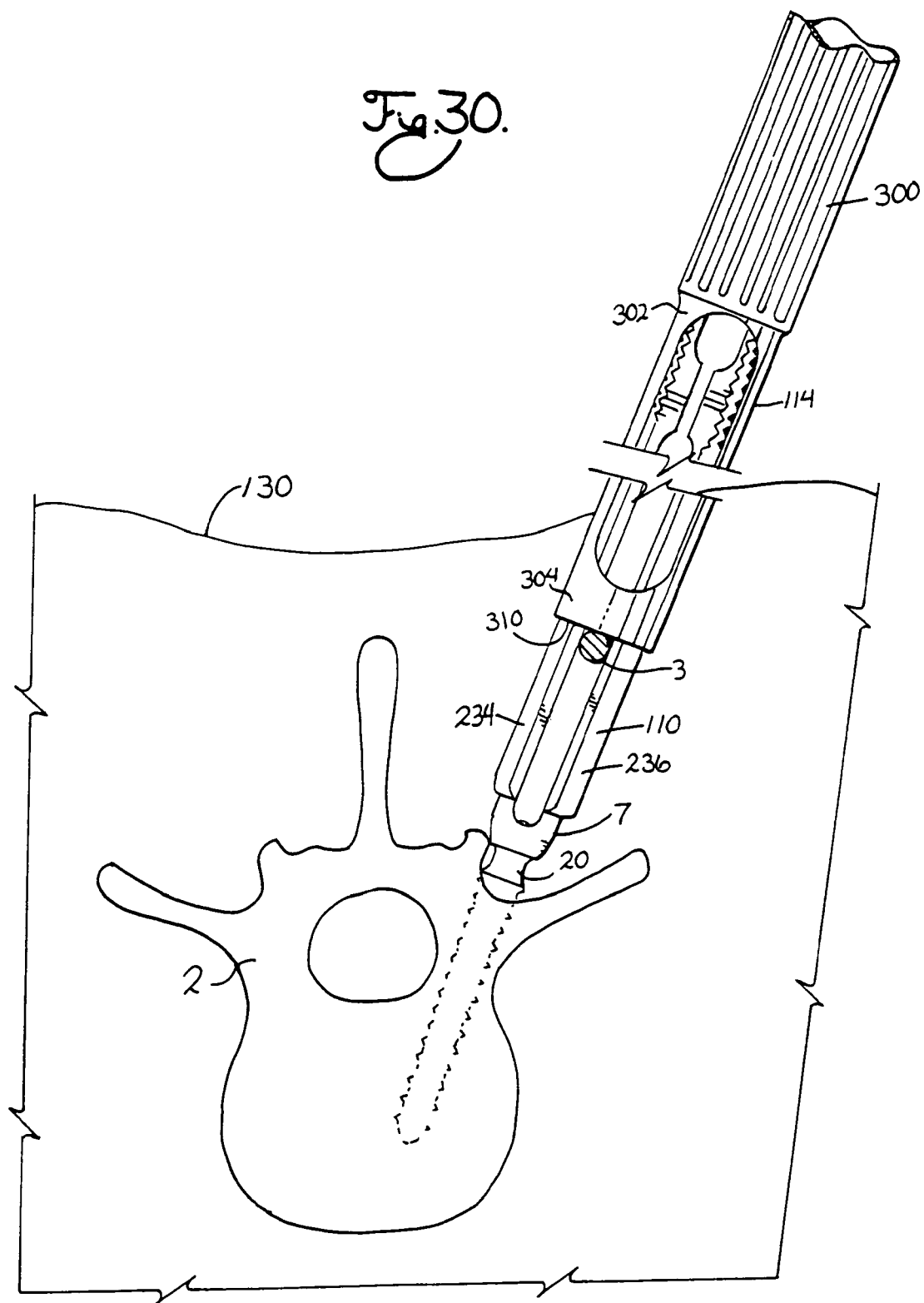

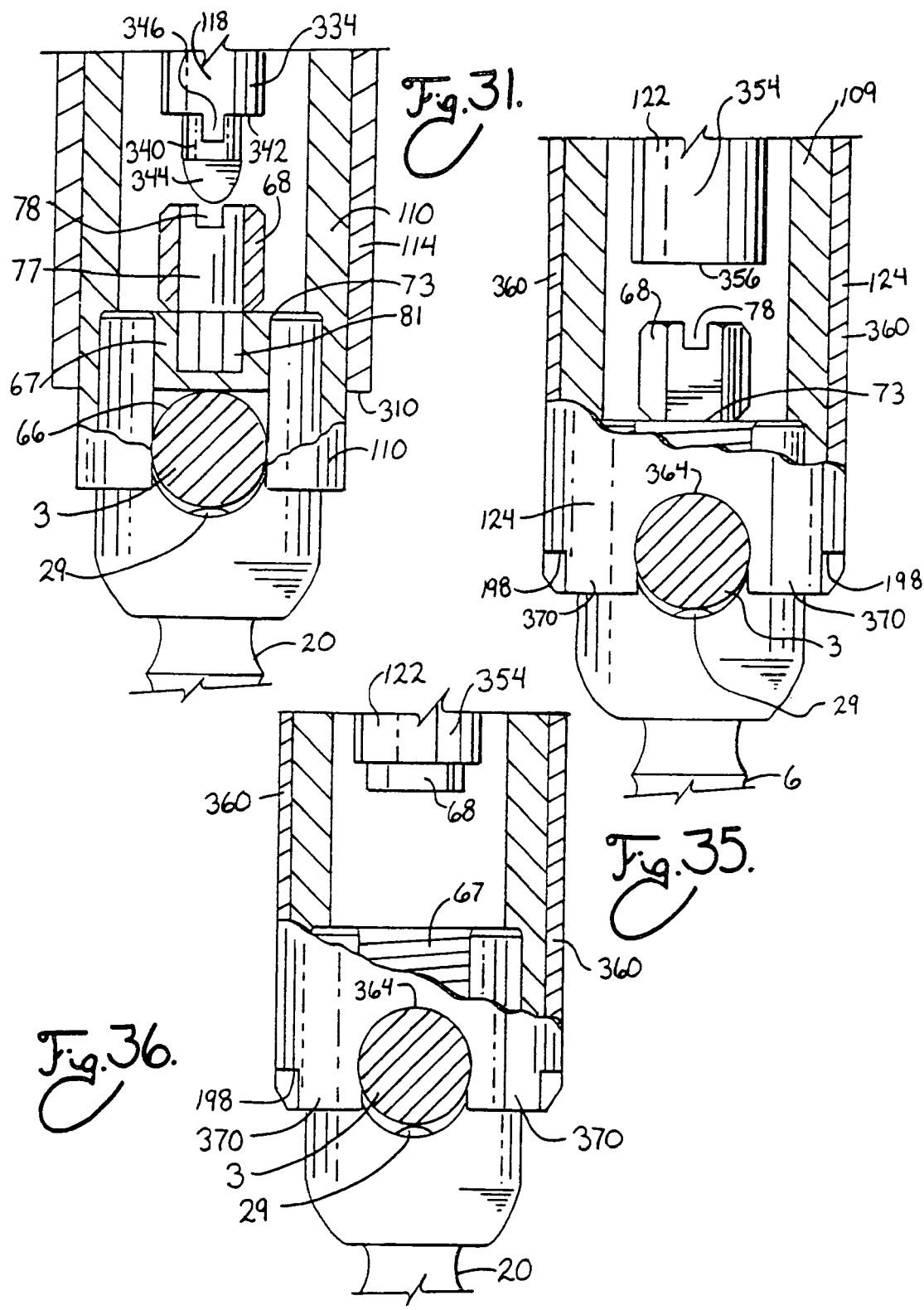

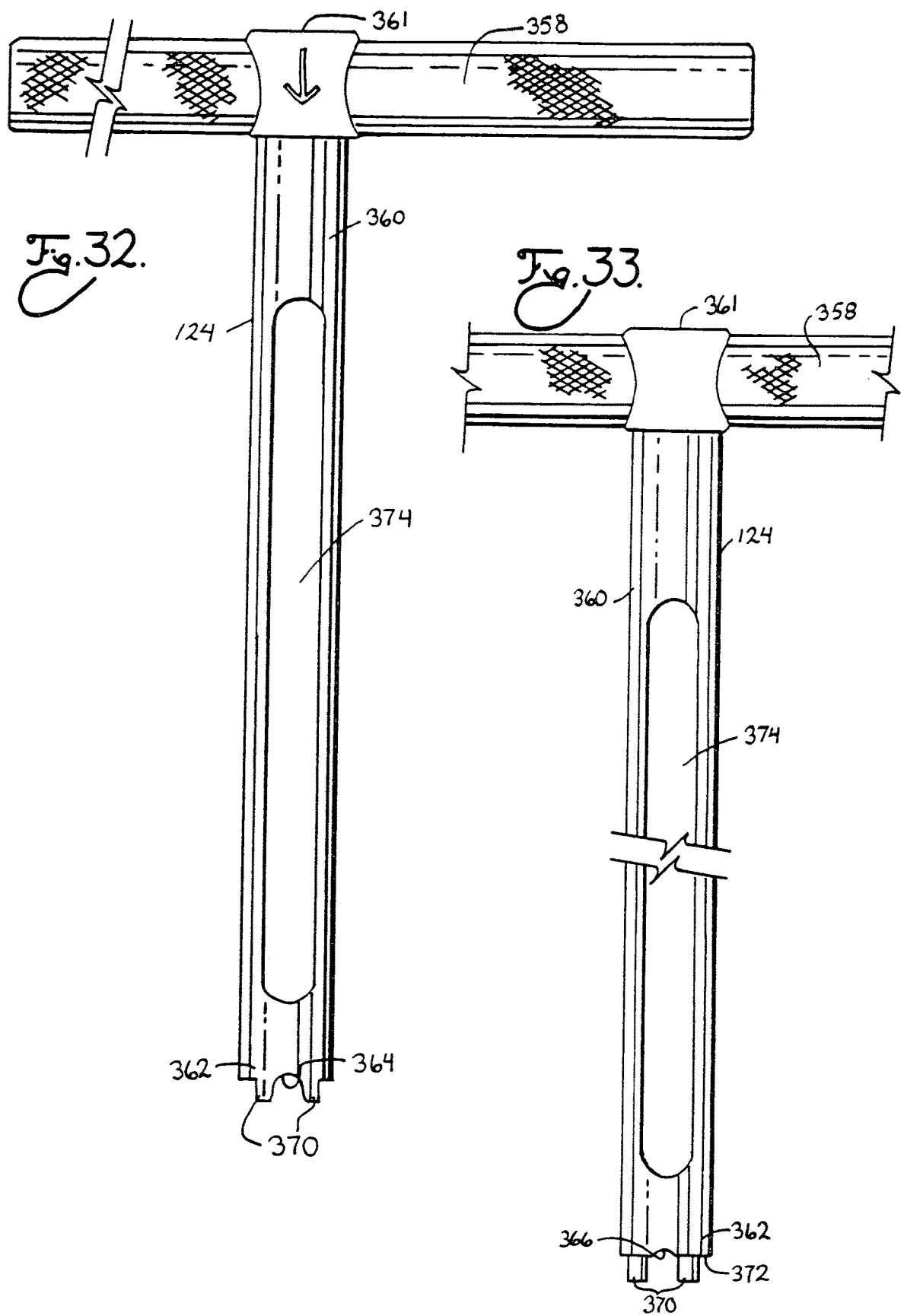

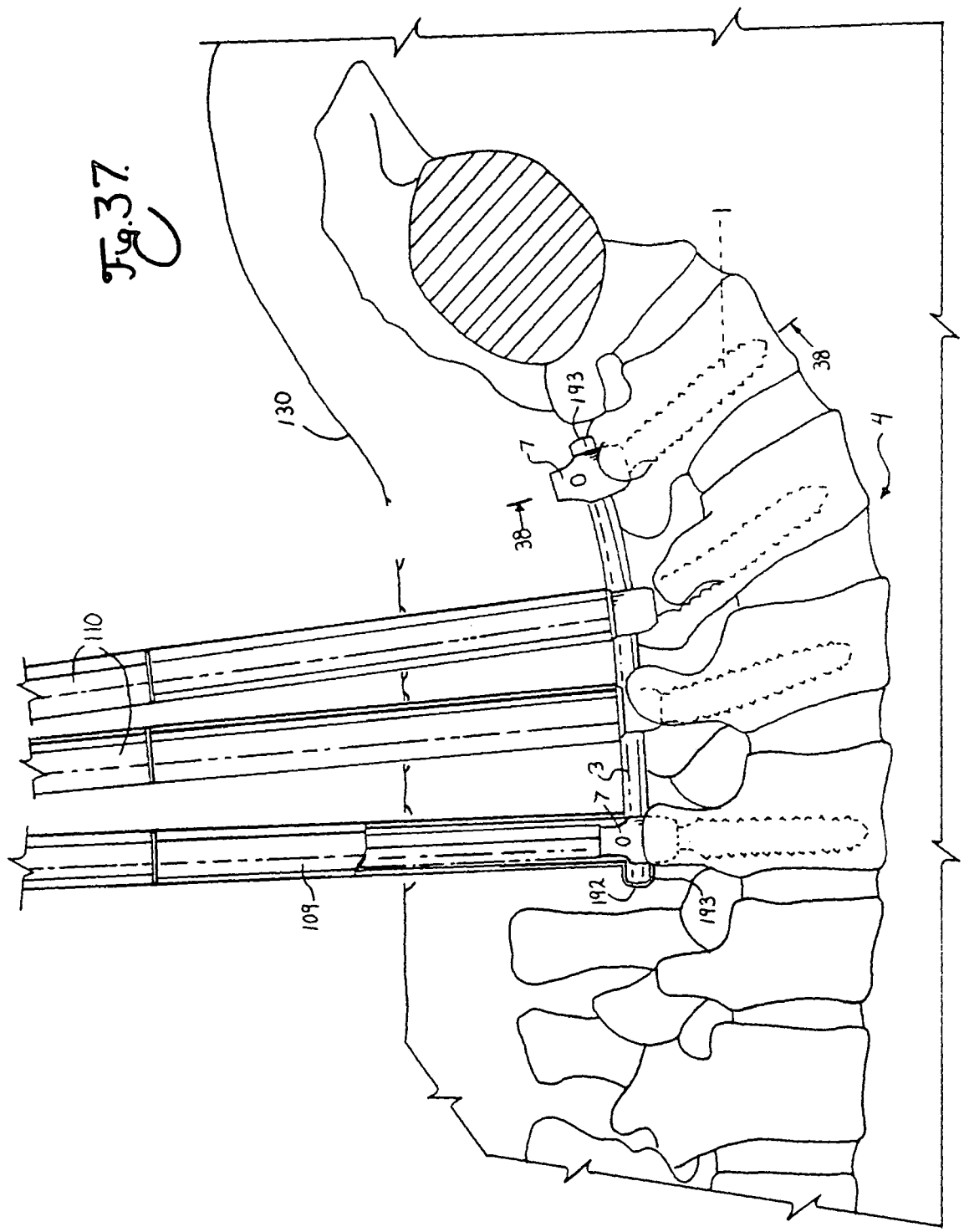

SPINAL FIXATION TOOL SET AND METHOD

CROSS-REFERENCE TO RELATED APPLICATIONS

This application is a continuation of U.S. patent application Ser. No. 14/968,623 filed Dec. 14, 2015, which is a continuation of U.S. patent application Ser. No. 12/924,223 filed Sep. 23, 2010, now U.S. Pat. No. 9,211,150, which is a continuation of U.S. patent application Ser. No. 10/996,289 filed Nov. 23, 2004, now U.S. Pat. No. 8,152,810 each of which is incorporated by reference in its entirety herein.

BACKGROUND OF THE INVENTION

The present invention relates to apparatuses and methods for use in performing spinal surgery and, in particular, to tools and methods of using such tools, especially for percutaneously implanting spinal screws and for implanting a rod for spinal support and alignment, using minimally invasive techniques.

For many years, spinal osteosynthesis apparatuses have been utilized to correct spinal deformities, injuries or disease. In such procedures, elongate rods are surgically attached to vertebrae of the spine to provide support and/or to realign or reposition certain vertebrae. Such rods are secured to vertebrae utilizing bone screws and other spinal implants. In order to reduce the impact of such surgery on the patient, a desirable approach is to insert such implants percutaneously or with surgical techniques that are minimally invasive to the body of the patient.

Problems arise when implantation tools designed for traditional surgery that is highly invasive are utilized in percutaneous surgery. The tools may be bulky, oversized or have irregular surfaces or protrusions. A projecting actuator arm or fastening member may be useful with respect to the spinal screw implantation process or the rod reduction process, but there is insufficient clearance to use such structure and/or such structure may produce additional invasive trauma which the percutaneous surgery is attempting to avoid.

A percutaneous procedure also presents a problem with implantation of rods that are elongate and have historically required a long incision and open wound in order to provide for the length of the rod and the space required for the surgeon's hands to manipulate the rod. Such problems are then compounded by the implants and insertion tools used with the rod.

Consequently, it is desirable to develop apparatuses and techniques that allow for the insertion of bone screws, the insertion and reduction of a rod into the bone screws and the securing of the rod to the bone screws with significantly less invasion into the body of the patient and with minimal surgical incision of the skin over the operational site.

SUMMARY OF THE INVENTION

A tool set according to the invention is provided for percutaneously implanting bone screws and an associated spinal rod in a patient. The tool assembly includes first and second end guide tools, each guide tool having an elongate body, an outer surface and a channel with a lateral opening extending through the outer surface and along a longitudinal axis an entire length of the guide tool. The channel and channel opening are sized and shaped for side loading and receiving of an end of the rod and also for receiving spinal implant fasteners and cooperating manipulation tools.

Near a bottom of the end guide tool body is a rigid, rod holding structure disposed opposite the lateral opening. The rigid rod holding structure projects laterally outwardly from the elongate body outer surface, and is sized and shaped to closely receive and abut against an end of the rod. The rod holding structure holds the rod end at a location outside of the spinal implant. The structure preferably includes a pair of spaced arms extending laterally about the end guide tool body. The guide tool body defines an opening disposed adjacent the arms, with the opening sized and shaped to receive the rod therethrough.

A tool set according to the invention may also include one or more intermediate guide tools, each having first and second elongate legs defining an elongate through-slot sized and shaped for receiving a rod therethrough.

Both the end guide tools and the intermediate guide tool have opposed spinal implant engaging structure disposed near a bottom thereof. The implant engaging structure of the illustrated embodiment includes first and second opposed radially inwardly projecting pins. The pins are sized and shaped to be received in cooperating apertures in the spinal implant for releaseable attachment thereto. Preferably each pin has an upwardly projecting lip sized and shaped to be received in an upwardly projecting inner recess of the spinal implant aperture, allowing for a snap-on, snap-off cooperation between the guide tool and the spinal implant.

To provide such a snap-on, snap-off cooperation between the end guide tool and a spinal implant, each end guide tool includes a narrow slot disposed opposite the lateral opening. The narrow slot and lateral opening cooperate to allow manual flexing of the guide tool body to increase a distance between the first and second pins during insertion and removal of the guide tool on the spinal implant.

A tool set of the invention further includes a driving tool attachable to both the end and intermediate guide tools. The driving tool is receivable in the tools and operably attachable to the spinal implant for rotating and driving the implant into bone. In an embodiment according to the invention, the end and intermediate guide tools have outer guide and advancement structure, such as a thread at an upper portion of the tool body. The driving tool has a fastener, a stem and a driving structure disposed at a lower end of the stem, the driving structure for rotating and driving the implant into bone. The fastener is freely rotatable with respect to the stem and includes an inner guide and advancement structure that is rotatingly mateable with the outer guide and advancement structure of the guide tools.

The tool set further includes a rod pusher attachable to both the end and intermediate guide tools. The rod pusher includes a sleeve and a driving end. The sleeve is receivable over the elongate guide tool body and operably attachable to the body for rotating thereabout, with the rotational movement of the sleeve also translating the driving end along the body. The rod pusher includes an inner guide and advancement structure mateable with the outer guide and advancement structure of the respective guide tool.

The tool set may also include an elongate torquing tool having a handle and a stem receivable in the channel of both the end and intermediate guide tools and attachable to an implant fastener. Cooperating with the torquing tool is an elongate anti-torque tool having a handle and a sleeve receivable over the respective guide tool body. The sleeve is sized and shaped to seat upon and abut against a rod at either side of the guide tool body, resisting any rotational movement of the anti-torque tool relative to the end guide tool.

A vertebral support rod implantation kit according to the invention, adapted for use with a plurality of vertebrae, includes a plurality of polyaxial bone screws, each bone screw being adapted for implantation in one vertebra, each of the bone screws having an attachment structure. The kit also includes an elongate rod having first and second ends, the rod sized and shaped to extend between a pair of end bone screws of the plurality of bone screws. The kit further includes a plurality of closure tops with each closure top being sized and shaped to mate with a respective bone screw and capture or retain the elongate rod within a cavity or channel defined by the respective arms of the bone screw. Additionally, the kit includes a pair of end guide tools, and may include one or more intermediate guide tools, each guide tool being attachable to the driver and the rod pusher previously described herein.

In a method according to the invention, a spinal fixation tool assembly is assembled by first attaching a bone screw head of a spinal implant screw to a mating attachment structure disposed at a first end of an elongate guide tool implant engaging member, the guide tool defining a laterally opening channel and having a second attachment structure disposed at a second end thereof. A driver is then inserted in the guide tool and attached spinal implant screw. The driver includes a fastener that is rotated in a first direction to mate the driver with the second attachment structure on the guide tool and thereby engage the driver with the spinal implant screw.

A method according to the invention includes the steps of inserting the attached driver, guide tool and spinal implant screw into an incision, especially a minimally invasive incision sized to snugly or closely receive the assembled tools and bone screw, and into contact with a vertebra, followed by turning the driver handle. By turning the handle, only the driver and the screw are rotated, driving the spinal implant screw into the vertebra.

Further method steps according to the invention include detaching the driver from the guide tool and attaching a rod pusher onto the guide tool by placing the rod pusher sleeve onto the guide tool and rotating the sleeve. The rod is then guided into and through all the guide tool channels. The sleeve is rotated, advancing a rod pushing end toward the bone screw and pushing the rod toward the screw until the ends of the rod are in contact with the laterally extending, rigid rod holding structure disposed near the bottom of the end guide tools. The method further includes the step of fixing closure tops to the spinal implant screw heads, with the rod being captured between the spinal implant screw and the closure top.

Objects and Advantages of the Invention

Therefore, objects of the present invention are: to provide a compact tool assembly for supporting and installing bone screws and other implants with minimal surgical invasion to the patient; to further provide a set of tools for implanting a spinal rod for support or alignment along a human spine with minimal surgical invasion of the patient; to provide such a set of tools including a pair of end tool guides for slidably guiding opposed ends of the rod toward end bone screws attached to the end guide tools; to provide such a set of tools including intermediate guide tools for each intermediate bone screw that guide the rod in slots therethrough to respective bone screws; to provide such a set of tools including rod and implant fastener or closure top installation tools for assisting in securing the rod in the bone screws; to provide such a set of tools wherein the guide tools are easily attached to and disengaged from the bone screws; to provide such a set of tools wherein the guide tools, guide tool supports or stabilizers, deployment tools, rod reduction tools, bone screw installation tools and implant fastener installation tools are all easily aligned, positioned, and engaged, if necessary, with respect to the bone screw and are disengaged from the bone screw and other tools in the installation assembly by manual manipulation of the surgeon outside the patient's skin; to provide a method of implanting a rod into bone screws within a patient with minimal surgical invasion of the patient; to provide such a method utilizing the previously described tools for percutaneous implantation of such a rod; and to provide such a set of tools and methods that are easy to use and especially adapted for the intended use thereof and wherein the tools are comparatively inexpensive to produce.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a front elevational view of an end guide tool according to the invention.

FIG. 2 is a side elevational view of the end guide tool of FIG. 1.

FIG. 3 is a rear elevational view of the end guide tool of FIG. 1.

FIG. 4 is a front elevational view of an intermediate guide tool according to the invention.

FIG. 5 is a side elevational view of the intermediate guide tool of FIG. 4.

FIG. 6 is a rear elevational view of the intermediate guide tool of FIG. 4.

FIG. 7 is an enlarged bottom plan view of the intermediate guide tool of FIG. 4.

FIG. 8 is an enlarged partial cross-sectional view taken along the line 8-8 of FIG. 4.

FIG. 9 is an enlarged cross-sectional view taken along the line 9-9 of FIG. 8.

FIG. 10 is an enlarged exploded perspective view of a polyaxial bone screw of the invention including a shank, head, retaining ring and nut.

FIG. 11 is an enlarged cross-sectional view of the head, taken along the line 11-11 of FIG. 10, illustrating the retaining ring being inserted into the head.

FIG. 12 is an enlarged cross-sectional view of the head similar to FIG. 11, shown with a retaining ring of FIG. 10, shown in cross-section, disposed in the head and seated on the shank upper end, and also shown partially exploded with a nut of FIG. 10, prior to the nut being rotatably inserted onto the shank upper end.

FIG. 16 is a fragmentary front elevational view of a driver according to the invention.

FIG. 17 is a fragmentary side elevational view of the driver of FIG. 16.

FIG. 18 is a fragmentary rear elevation view of the driver of FIG. 16 having a portion shown in cross-section, taken along the line 18-18 of FIG. 17.

FIG. 19 is a reduced and fragmentary view of the driver of FIG. 18 shown cooperating with the intermediate tool and attached bone screw (the intermediate tool shown in cross-section, similar to FIGS. 13-15, but taken along an entire length thereof).

FIG. 20 is an enlarged and fragmentary view, similar to FIG. 19, showing the driver spaced from the shank assembly.

FIG. 21 is an enlarged and fragmentary view, similar to FIG. 20, showing the driver engaging the shank assembly.

FIG. 26 is an enlarged perspective view of a spinal implant fastener according to the invention.

FIG. 27 is a reduced exploded view of an assembly according to the invention including the implant fastener of FIG. 26 attached to a manipulation tool, the rod pusher of FIG. 23 and the intermediate guide tool of FIG. 4 with attached bone screw.

FIG. 28 is a reduced view, showing the manipulation tool and implant fastener of FIG. 27 inserted in a rod pusher, intermediate guide tool and bone screw assembly, the rod pusher in cross-section, taken along the line 28-28 of FIG. 24, the intermediate guide tool in cross-section, similar to the line 13-13 of FIG. 5, but extending along the entire length of the tool, and the bone screw in front elevation.

FIG. 29 is a partial and generally schematic view of a patient's spine, showing a pair of end tools with a rod contained therebetween and a pair of intermediate tools of the present invention with one of the intermediate tools shown with an attached rod pusher in a rod reduction application, with one of the end guide tools shown partially cut-away, illustrating an implant fastener manipulation tool disposed within the end tool and cooperating with an implant fastener, the tools being utilized in an early stage of rod implantation to guide the rod toward the bone screws.

FIG. 30 is an enlarged, partial and generally schematic cross-sectional view taken along the line 30-30 of FIG. 29.

FIG. 31 is an enlarged and partial view, similar to FIG. 28, further showing the implant fastener in cross-section, taken along the line 31-31 of FIG. 26, with the implant fastener installed in the bone screw and the manipulation tool being moved away therefrom.

FIG. 32 is a partial, front elevational view of an anti-torque tool according to the invention.

FIG. 33 is a partial, rear elevational view of the anti-torque tool of FIG. 32.

FIG. 35 is an enlarged and partial view of the assembly of FIG. 34, with portions removed to show the detail thereof, shown prior to torquing of the implant fastener.

FIG. 36 is an enlarged and partial view similar to FIG. 35 shown subsequent to torquing, with the torquing tool removing a break-off head of the implant fastener.

FIG. 37 is a partial and generally schematic view of a patient's spine, similar to FIG. 29, with one of the end guide tools removed and the other end guide tool shown partially cut-away, illustrating the rod installed in the bone screws and abutting against a holding structure of the end tool.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

With reference to FIGS. 1-38, the reference letter T generally designates a tool set according to the present invention made up of a number and variety of tool assemblies for use in installing a set of bone screws 1 into vertebrae 2, followed by the installation of an orthopedic spinal rod or longitudinal member 3 into the bone screws 1 along a patient's spine 4 in a process according to the present invention.

Figure 22:
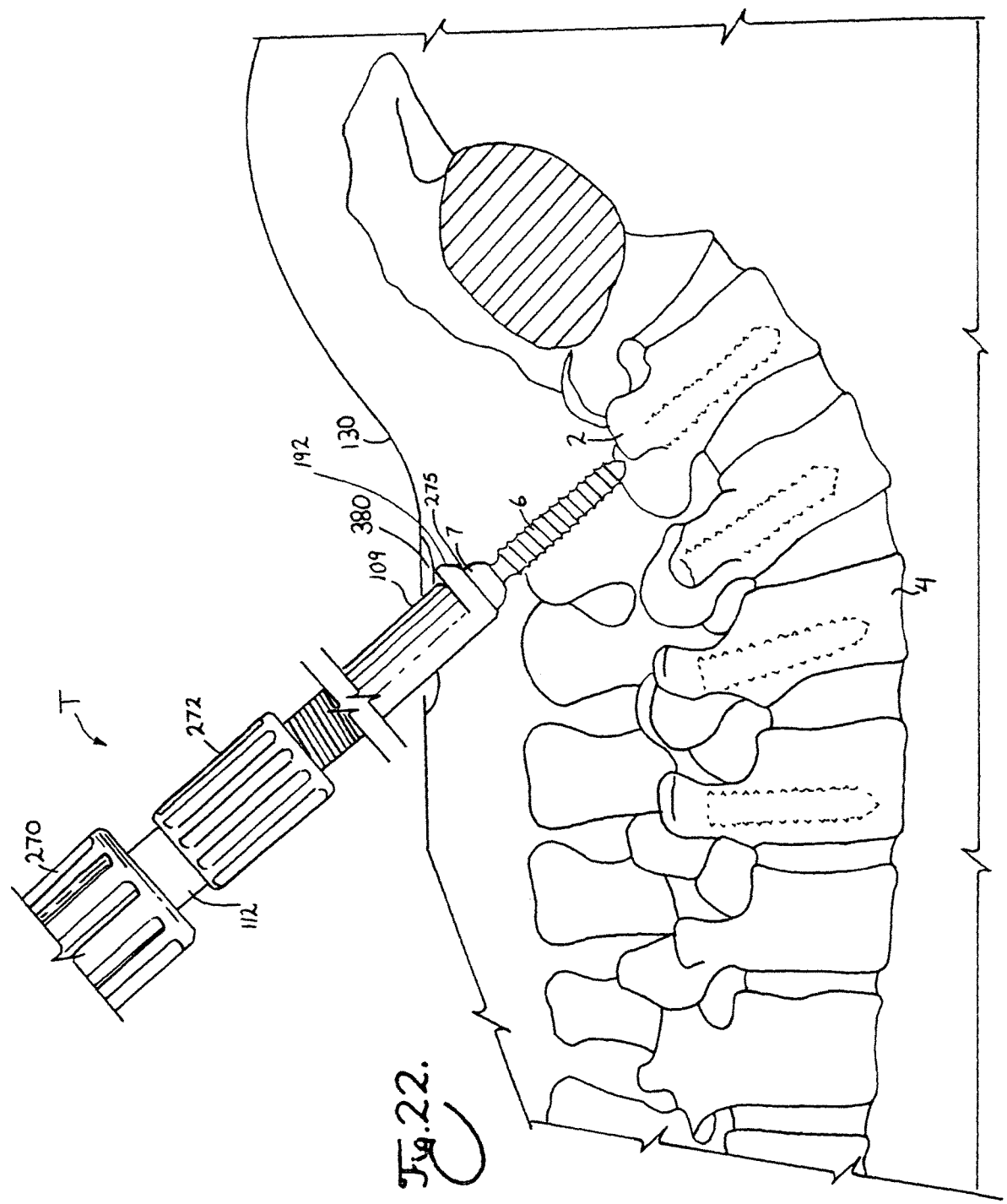
FIG. 22 is a partial, fragmentary and generally schematic view of a patient's spine showing a driver of FIG. 16 cooperating with an end tool of FIG. 1 with attached bone screw being guided toward a threaded bore in a vertebra in an early stage of a method according to the invention.

With special reference to FIGS. 10-12 and 38, the reference numeral 1 generally represents a polyaxial bone screw apparatus or assembly utilized in the present invention. However, it is foreseen that a variety of bone screws may be utilized with the other components of the tool set T of the invention, as will be discussed more fully below. In the illustrated embodiment, the bone screw assembly 1 includes a shank 6, a head 7, a retaining structure or ring 8, a fastener or nut 9 and a closure structure or top 10. The nut 9 includes an inner raised helical rib or thread 12, an external hexagonally faceted surface 13 and a slightly radiused or curved top surface 14. The shank 6 is elongate and has a lower body 15. As illustrated in FIG. 19, the shank body 15 has a helically wound bone implantable thread 17 extending from near a top 18 to near a tip 19 of the body 15 and extending radially outward therefrom. During use, the body 15 utilizing the thread 17 is implanted into the vertebra 2, as is shown in FIG. 22. The shank 6 also has an elongate axis of rotation A. It is noted that the reference to the words top and bottom, upper and lower, and the like, as used herein refers to the alignment shown in the various drawings, as well as the normal connotations applied to such devices, and is not intended to restrict positioning of the bone screw 1 and other tools of the tool set T of the invention in actual use.

Extending axially outward and upward from the shank body 15 is a neck region 20, substantially hyperboloid in configuration, having a minimum radius smaller than a radius at the top 18 of the body 15. Further extending axially and outwardly from the neck 20 is a capture structure 21 providing a connective or capture portion of the shank 6. The neck region 20 provides a space between the capture structure 21 and the shank body 15, operably also spaced from the bone or vertebra 2 for adjoining with the head 7. The capture structure 21 has a radially outer cylindrical surface 22 with an external helically wound guide and advancement structure illustrated as a rib or thread 24. The thread 24 is located near an upper end 25 of the shank 6 and is sized and shaped to receive the threaded nut 9. Although a simple raised helical rib or thread 24 is shown in the drawings, it is foreseen that other structures including other types of threads, such as buttress and reverse angle threads, and non-threads, such as helically wound flanges with interlocking surfaces, may be used in alternative embodiments of the present invention.

Figure 38:
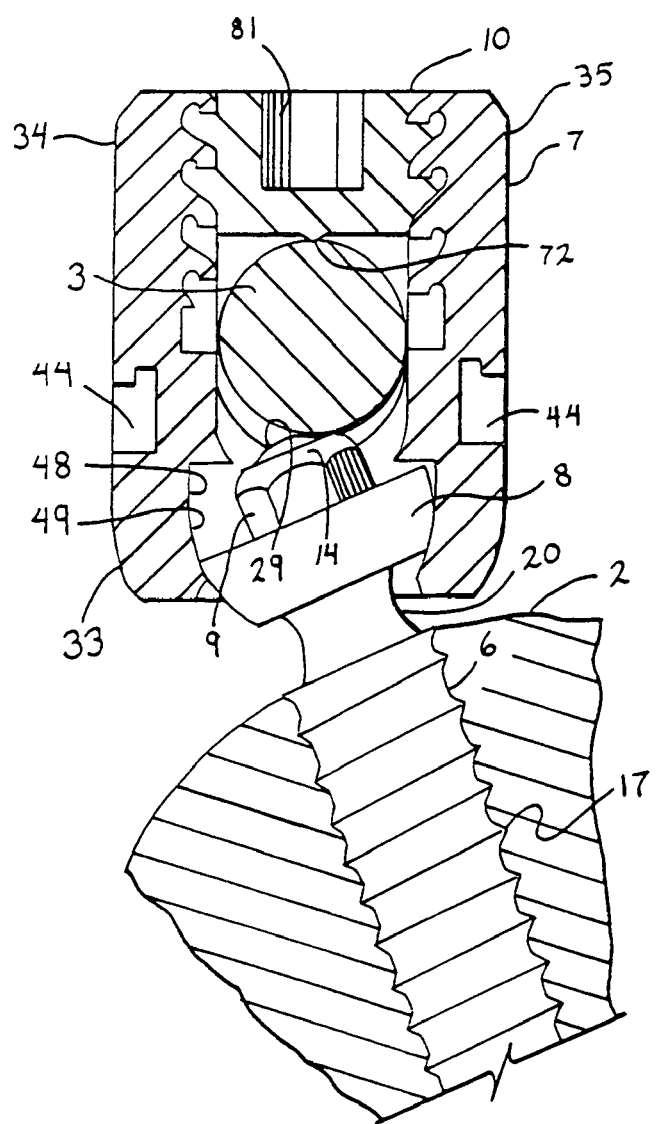
FIG. 38 is an enlarged cross-sectional view taken along the line 38-38 of FIG. 37 with the bone screw shown in front elevation.

Also located at the shank upper end 25 is a centrally located, axially extending and upwardly directed projection or dome 29 that is centrally radiused so as to have a first radius. The projection 29 is preferably curved or dome-shaped as shown in the drawings, for positive engagement with the rod 3, when the bone screw assembly 1 is assembled, as shown in FIG. 38, and in any alignment of the shank 6 relative to the head 7. In certain embodiments, the surface 29 is smooth. While not required in accordance with practice of the invention, the domed surface 29 may be scored or knurled to further increase frictional engagement between the dome 29 and the rod 3. Also as illustrated in FIG. 38, preferably the nut top surface 14 has the same or similar first radius as the dome 29 to provide a continuous, positive engagement with the rod 3 at any alignment of the shank 6 with respect to the head 7.

Disposed between the neck 20 and the threads 24 of the capture structure 21 is a smooth cylindrical surface 30 terminating at a lower shoulder 31. The shoulder 31 is disposed adjacent to the neck 20 and includes an annular seating surface 32 oriented perpendicular to the axis of rotation A. The surface 32 extends outwardly radially from the cylindrical surface 30. The shoulder 31 divides the smooth cylindrical surface 30 from the neck 20 of the shank 6. The cylindrical surface 30 has a reduced inner radius relative to a maximum radius of the neck 20 adjacent the shoulder 31. The cylindrical surface 30 is sized and shaped to slidingly mate with the retaining ring 8 and centrally position the retaining ring 8 in alignment with the shank axis A and also generally centrally within the head 7, as will be discussed more fully below.

The head 7 has an outer profile that is substantially cylindrical in shape, as shown in FIG. 10. However, the head 7 is not a solid cylinder, but rather includes inner openings, a cavity and a channel described more fully hereafter, and being substantially symmetrical with respect to an axis of rotation B of the head 7. The head 7 includes a base 33 integral with a pair of upstanding arms 34 and 35. The arms 34 and 35 form a U-shaped channel 38 therebetween, defined in part by a lower seat 39 having substantially the same radius as the rod 3 for operably snugly receiving the rod 3. Each of the arms 34 and 35 has an interior surface 41 that includes a partial, helically wound guide and advancement structure 42. In the illustrated embodiment, the guide and advancement structure 42 is a partial helically wound flangeform configured to mate under rotation with a similar structure on the closure top 10, as described more fully below. A suitable locking guide and advancement structure of this type is disclosed in U.S. Pat. No. 6,726,689 from Ser. No. 10/236,123 which is incorporated herein by reference.

However, it is foreseen that the guide and advancement structure 42 could alternatively be a V-shaped thread, a buttress thread, a reverse angle thread or other thread like or non-thread like helically wound advancement structure for operably guiding under rotation and advancing the closure top 10 between the arms 34 and 35.

Tool engaging apertures 44 are formed on outer surfaces of the arms 34 and 35 for holding the head 7 during assembly and also during the implantation of the shank body 15 into the vertebra 2. The apertures 44 are disposed opposite one another and each include respective upwardly projecting, hidden inner recesses 45 for cooperating with complimentary bone screw holding components of guide tools according to the invention, discussed more fully below. It is noted that the apertures 44 and the cooperating guide tool holding components may be configured to be of a variety of sizes and locations for attachment to the guide tool along any of the surfaces of the arms 34 and 35.

A chamber or cavity 47 is located within the head base 33 that opens upwardly into the U-shaped channel 38. The cavity 47 is defined in part by a partially spherically shaped inner surface 48, at least a portion of which forms a partial internal hemispherical seat 49. The surface or seat 49 is sized and shaped for mating with the retaining ring 8, as described more fully below. The hemispherically shaped surface 49 has a second radius associated therewith. At the opening into the U-shaped channel 38, the cavity 47 is defined in part by a discontinuous shoulder or upper coplanar seat 50 disposed on each of the arms 34 and 35 extending radially and substantially perpendicular to the axis B, as illustrated in FIG. 11.

At a bottom of the base 33, the cavity 47 communicates with a substantially circular bore 52 opening to an exterior of the base 33. The bore 52 is coaxial with the rotational axis B of the head 7. The bore 52 is defined at least in part by a restrictive neck 54 that has a radius that is smaller than an outer radius of the ring 8, as will be discussed further below, so as to form a restrictive constriction at the location of the neck 54 relative to the retaining ring 8 to prevent the ring 8 from passing between the cavity 47 and the lower exterior of the base 33 of the head 7. However, it is foreseen that the retaining ring 8 could be compressible and thus loadable through the neck 54 and then allowed to expand and fully seat in the spherical seating surface 49. A bevel 55 extends between the neck 54 and the bottom exterior of the base 33.

The retaining ring 8 is used to retain the capture structure 21 of the shank 6 within the head 7. The retaining ring 8, best illustrated in FIGS. 10-12, has an operational central axis that is the same as the elongate Axis A associated with the shank 6, but when the retaining ring 8 is separated from the shank 6, the axis of rotation is identified as axis C, as shown in FIG. 10. The ring 8 has a central bore 57 disposed along the central axis C, with the central bore 57 passing entirely through the retaining ring 8 from a top surface 58 to a bottom surface 59 thereof. The bore 57 is sized and shaped so that the ring 8 fits snugly but slidably over the shank capture structure 21 and outer cylindrical surface 30 in such a manner as to allow sliding axial movement therebetween under certain conditions, as described below. A surface 60 defining the bore 57 is smooth and has a radius configured to be only slightly larger than an outer radius of the cylindrical surface 30, providing for slidable mating engagement between the surface 60 and the surface 30. As will be described subsequently in more detail, the shank capture structure 21 is uploadable into the head 7, and through the ring 8 that is already disposed in the head 7, by axially sliding the capture structure 21 through the ring central bore 57 until the ring bottom surface 59 is seated on the annular surface 32 of the shank 6, as illustrated in FIG. 12.

To secure the retaining ring 8 within the head 7, the inner thread 12 of the nut 9 is mated to the outer thread 24 of the capture structure 21. Similar to the thread 24, although a simple raised helical rib or thread 12 is shown in the drawings, it is foreseen that other structures including other types of threads, such as buttress and reverse angle threads, and non-threads, such as helically wound flanges with interlocking surfaces, may be used in alternative embodiments of the present invention.

Figure 13:
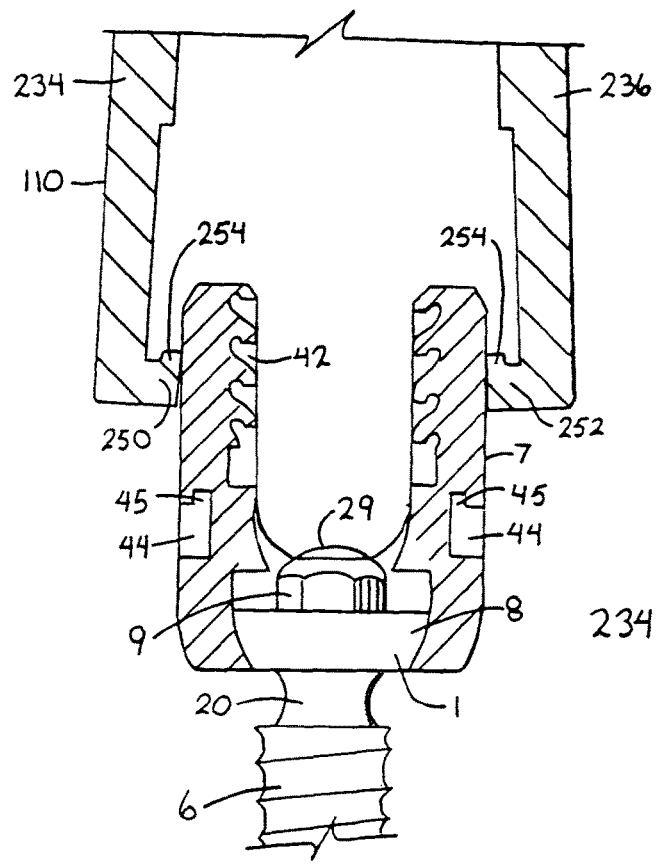
FIG. 13 is an enlarged cross-sectional view of the head similar to FIG. 11, shown with an assembled shank, retaining ring and nut, and further showing the intermediate tool in cross-section, taken along the line 13-13 of FIG. 5, in a first stage of a snap-on attachment to the head.

The mating of the nut inner thread 12 and the capture end outer thread 24 is aided by the shoulder 50 of the head 7. As illustrated in FIG. 12, after receiving the retaining ring 8 thereon, the shank 6 may be moved upwardly, until the top surface 58 of the ring 8 abuts the flat shoulder 50 at each of the arms 34 and 35, providing a relatively stable position for receiving the nut 9. The nut 9 is then top loaded into the head 7 through the channel 38, placed in axial alignment with the shank 6, lowered onto the shank capture structure 21, and rotated in a clock-wise direction when viewed from above. The nut 9 may be installed with a socket-type tool, similar to a driver 112 shown in FIGS. 16-21 utilized for implanting the bone screw assembly 1 in a vertebra 2, and discussed more fully below. The socket-type tool mates with the external faceted hexagonal surface 13, and is rotated and driven downward until the bottom surface 59 of the ring 8 abuts the annular surface 32 of the lower shoulder 31 and is frictionally fixed thereto. When the ring 8 abuts the annular surface 32, the dome 29 protrudes axially above the nut 9 with the nut top surface 14 disposed contiguous to the dome 29. The dome 29 and the top surface 14 preferably forming a continuous curved perimeter, the surface 14 extending the first radius of the dome 29, as illustrated in FIG. 13.

To further ensure frictional engagement between the nut 9 and the capture structure 21 of the shank 6, the nut 9 includes one or more weakened areas 61 located along the faceted surface 13 thereof, as shown in FIG. 12. A set tool (not shown) having a tip passes between the upstanding arms 34 and 35 of the head 7 and pushes against the nut 9 at the weakened area 61, the tip indenting the area 61, forming an indentation or deformation on the nut surface, and also pressing against the thread 12 and/or the thread 24, creating or causing a deformed thread portion or portions, interlocking the threads 12 and 24, which in turn lodges the ring 8 in a fixed position with respect to the shank 6. The deformed thread portion or portions prevent counter-clockwise rotation of the nut 9 with respect to the shank capture structure 21, and thus prevents the nut 9 and the ring 8 from migrating up and off the shank upper end 25 and into the channel 38, away from the desired position within the head 7.

The ring 8 has a radially outer partially hemispherically shaped surface 65 sized and shaped to slidingly mate with the partially hemispherically shaped seating surface 49. The surface 65 has a third radius approximately equal to the second radius associated with the seating surface 49. The third radius of the ring surface 65 is substantially larger than the first radius associated with the dome 29 and also substantially larger than an inner radius of the neck 54. Although not required, it is foreseen that the outer partially spherically shaped surface 65 may be a high friction surface such as a knurled surface or the like.

Preferably, the retaining ring 8 is constructed of a metal or other material having sufficient resilience and elasticity so as to allow the ring 8 to radially expand slightly outward by downward pressure of the nut 9 on the top surface 58 and under pressure from structure above, as will be discussed further below. This produces a slight outward radial expansion in the ring 8 at the shoulder 31 of the shank 6.

The longitudinal member or elongate rod 3 can be any of many different types of implants utilized in reconstructive spinal surgery and the like, but is normally a cylindrical elongate structure having a smooth, cylindrical surface 66 of uniform diameter. The rod 3 is preferably sized and shaped to snugly seat near the bottom of the U-shaped channel 38 at the lower seat 39 and, during normal operation, will be positioned slightly above a bottom of the channel 38. In particular, the rod 3 normally engages the shank dome 29, as illustrated in FIG. 38, and urges against the dome 29 and, consequently, downwardly against the shank 6 when the bone screw assembly 1 is fully assembled. For this to occur, the shank domed surface 29 must extend at least slightly into the space of the channel 38 when the retaining ring 8 is snugly seated in the lower seat 49 of the head cavity 47. The shank 6 and retaining ring 8 are thereby locked or held in position relative to the head 7 by the rod 3 firmly pushing downward on the shank domed surface 29. At certain degrees of inclination of the shank 6 with respect to the head 7, the rod 3 may push downward on both the domed surface 29 and a portion of the nut top surface 14.

With particular reference to FIGS. 26, 31 and 38, the implant fastener or closure top 10 can be any of a variety of different types of closure structures for use in conjunction with the present invention with suitable mating structure on the inner or outer surfaces of the upstanding arms 34 and 35 of the bone screw head 7. The closure top 10 is rotatably received between the spaced arms 34 and 35.

The illustrated closure top 10 has a generally cylindrical shaped base 67 with an upwardly extending break-off head 68. The base 67 includes a helically wound guide and advancement structure 71 that is sized, shaped and positioned so as to engage the guide and advancement structure 42 on the arms 34 and 35 to provide for rotating advancement of the closure structure 10 into the head 7 when rotated clockwise and, in particular, to cover the top or upwardly open portion of the U-shaped channel 38 to capture the rod 3, preferably without splaying of the arms 34 and 35.

The base 67 further includes a lower point or projection 72. The projection 72 provides for increased friction against the rod 3. The closure structure 10 operably biases against the rod 3 at and near the projection or point 72 by advancement and applies pressure to the rod 3 under torquing, so that the rod 3 is urged downwardly against the shank domed top surface 29 that extends into the channel 38. Downward biasing of the shank top surface 29 operably produces a frictional engagement between the rod 3 and the surface 29 and also urges the retaining ring 8 toward the base 33 of the head 7, so as to frictionally seat the retaining ring spherical surface 65 fixedly against the partial internal spherical seating surface 49 of the head 7, also fixing the shank 6 and retaining ring 8 in a selected, rigid angular position relative to the head 7.

The closure structure break-off head 68 is secured to the base 67 at a neck 73 that is sized and shaped so as to break away at a preselected torque that is designed to properly seat the retaining ring 8 in the head 7. The break-off head 68 includes an external faceted surface 75, a central bore 77 and a pass-through slot 78 for receiving a manipulation tool 118 more fully described below. The faceted surface 75 is sized and shaped to receive a conventional mating socket type head of a torquing tool 122 to rotate, drive and torque the closure structure 10, also more fully described below. It is foreseen that different driving heads or other methods of driving the closure top 10 may be utilized with certain embodiments of the invention, including non-break-off closure top designs.

The closure structure 10 also includes removal tool engagement structure which in the present embodiment is in the form of a hex-shaped and axially aligned aperture 81 disposed in the base 67, as shown in FIGS. 31 and 38. The hex aperture 81 is accessible after the break-off head 68 breaks away from the base 67. The aperture 81 is coaxial with the helically wound guide and advancement structure 71 and is designed to receive a hex tool, of an Allen wrench type, into the aperture 81 for rotating the closure structure base 67 subsequent to installation so as to provide for removal thereof, if necessary. Although a hex-shaped aperture 81 is shown in the drawings, the tool engagement structure may take a variety of tool-engaging forms and may include one or more apertures of various shapes, such as a pair of spaced apart apertures, or a left hand threaded bore, or an easy-out engageable step down bore, a hexalobular aperture (for example, sold under the TORX trademark), or other multi-lobular aperture or the like.

As shown in dotted lines in FIG. 11, prior to the polyaxial bone screw assembly 1 being placed in use according to the invention, the retaining ring 8 is typically first inserted or top-loaded, into the head U-shaped channel 38, and then into the cavity 47 to dispose the retaining ring 8 within the inner surface 48 of the head 7. As shown in FIG. 11, the retaining ring outer edge defined by the top surface 58 slides along the inner surface 48 until the top surface 58 clears the shoulder 50. Then, the retaining ring 8 is turned so as to be coaxial with the head 7 (the Axis C aligned with the Axis B), the top surface 58 facing the channel 38, and the surface 65 seated upon and in sliding engagement with the seating surface 49 as shown in solid lines in FIG. 2.

With reference to FIG. 12, the shank upper end 25 is then inserted or bottom-loaded into the head 7 through the bore 52 defined by the neck 54. The retaining ring 8, now disposed in the head 7 is coaxially aligned with the shank capture structure 21 at the upper end 25, so that the dome 29 passes through the bore 57 and the ring inner surface 60 is slidingly mated to the cylindrical surface 30 of the capture structure 21.

As shown in FIG. 12, the retaining ring 8 is preferably pushed upwardly into abutment with the shoulder 50 of the head 7 to provide ease in installment of the nut 9. The nut 9 is then downloaded through the channel 38 of the head 7, also as shown in FIG. 12, and then rotatingly mated with the helical thread 24 on the capture structure 21 of the shank 6, until the nut 9 abuts against the top surface 58 of the retaining ring 8. The position of the nut 9 on the shank 6 is then fixed by inserting the set tool (not shown) between the upstanding arms 34 and 35 of the head 7 and pushing against the nut 9 with the set tool tip at the weakened area 61, the tip indenting the area 61 and also pressing against the threads 12 and 24, creating a deformed thread portion or area, locking the nut 9 to the capture structure 21, which in turn lodges the ring 8 in a fixed position with respect to the shank 6. The deformed thread portion or portions prevent counter-clockwise rotation of the nut 9 with respect to the capture structure 21, and thus prevents the nut 9 and the ring 8 from migrating up and off the shank upper end 25.

At this time the shank 6 is in slidable and rotatable engagement with the head 7, while the capture structure 21, the nut 9 and the retaining ring 8 cooperate to maintain the shank body 15 in rotational relation with the head 7. Only the retaining ring 8 is in slidable engagement with the head spherical seating surface 49. Both the capture structure 21 and the threaded portion of the shank body 15 are in spaced relation with the head 7. The shank body 15 can be rotated through a substantial angular rotation relative to the head 7, both from side to side and from front to rear so as to substantially provide a universal or ball joint wherein the angle of rotation is only restricted by engagement of the neck 20 of the shank 6 with the neck 54 defining the bore 52 of the head. An example of such rotation is shown in FIG. 38. The bevel 55 provides for a slight increase in the extent of angular rotation of the shank body 15 with respect to the head 7.

The present invention is not intended to be restricted to a particular type of bone screw or bone screw closure mechanism. In the present embodiment, a polyaxial type bone screw 1 is utilized wherein the shank 6 is locked in position by direct contact with the rod 3. It is foreseen that the tool set T of the present invention can be used with virtually any type of bone screw, including fixed monoaxial and polyaxial bone screws of many different types wherein the head is locked relative to the shank by structure other than in the manner described in the illustrated embodiment.

The tool set T according to the invention typically includes at least one, but typically a pair of end guide tools 109 and up to a plurality of intermediate guide tools 110, each guide tool mateable with the bone screw 1 at the apertures 44. The guide tools 109 and 110 are also mateable with a driver 112 for implanting the bone screws 1 into vertebrae 2 of the patient's spine 4. The tool set T also includes a rod pusher 114, also mateable with the guide tools 109 and 110. The illustrated tool set T further includes an implant fastener manipulation tool 118, a torquing tool 122 and a cooperating anti-torque tool 124, each of which cooperates with both the guide tools 109 and 110.

As illustrated in FIG. 29, a tool set T of the illustrated embodiment may include a pair of end guide tools 109 and a pair of intermediate guide tools 110 disposed between the end guide tools 109 along a portion of a patient's spine 4, each guide tool 109, 110, attached to a bone screw 1. But it is noted that according to the invention, none, one or many intermediate guide tools 110 may be used, depending upon the particular application, so that one intermediate guide tool 110 is used for each intermediate bone screw 1 to which the rod 3 is to be attached. Rods 3 or other longitudinal members are often installed on both sides of the spine 4 during the same procedure.

The end guide tool 109 is illustrated in FIGS. 1-3, 22, 29, and 34-37. The elongate end guide tool 109 is somewhat cylindrical in outer profile. With respect to inner profile, the guide tool 109 forms a channel 126 with an elongate lateral opening of various widths, configured to receive, contain and allow translational movement along the channel 126, or rotational relative movement of certain tools, as described more fully below. The channel 126 extends from a top 128 to a bottom 129 of the guide tool 109, parallel to a central axis of rotation D thereof. The channel 126 is sized to accommodate elongate tools and bone screw components, such as the fastener or closure top 10.

In particular, each end guide tool 109 has an elongate body that is sized and shaped to be sufficiently long to extend from implanted bone screws 1 through an exterior of a patient's skin 130 so as to provide an outwardly extending and upper handle portion 132 that allows and provides for gripping by a surgeon during procedures utilizing the tool set T, with or without an attached driver 112 or rod pusher 114.

Each of the end guide tools 109 further includes an intermediate portion 134 and a lower implant engaging portion 136 which includes opposed implant engaging members for securing an implant or bone screw therebetween.

Each end guide tool 109 upper or handle portion 132 has a back wall with a substantially flat portion 138 joining a pair of substantially cylindrically shaped side walls 140 and 142. A lateral, generally elongate and axially extending opening 144 communicates with the channel 126, and opens at the top 128, forming a U-shaped cross-section, a C-shaped cross-section, a crescent shaped cross-section or the like, having a side-to-side width W near the top 128. The opening 144 widens to a side-to-side width of W' in a mid-section of the handle portion 132, substantially narrows to a side-to-side width of W" and then widens again to the width W at a lower section of the upper handle portion 132.

Along the length of the intermediate portion 134 and the implant engaging portion 135, the opening 144 has a substantially constant side-to-side width of W, and opens at the bottom 129. The width W is preferably slightly larger than a diameter of the rod or longitudinal member 3. The opening 144 is also preferably sufficiently wide to intermittently receive additional tools and/or a fastener, such as the closure top 10 for sideways loading into the channel 126.

Disposed on either side of the opening 144 are the substantially cylindrical side walls 140 and 142. On either side of the narrowest width W", are co-planar surfaces 148 and 150 integral to the walls 140 and 142, respectively. The co-planar surfaces 148 and 150 are parallel with the flat back wall surface portion 138. Although not required for the illustrated embodiment, it is foreseen that the surfaces 140 and 142, as well as the back wall portion 138, provide alignment surfaces when the guide tool 109 is utilized with other tools, such as certain bone screw drivers and rod pushers also having flat cooperating surfaces.

The upper handle portion 132 also includes an outer helically wound discontinuous guide and advancement structure 152 disposed on outer surfaces of both of the substantially cylindrically shaped side walls 140 and 142, which may include conventional helically wound V type threads, buttress threads, helically wound square threads, or other guide and advancement structure to cooperate with equivalent or mateable structure within the driver 112 and the rod pusher 114, as described more fully below. The guide and advancement structure 152 extends from near the intermediate portion 134 to the top or upper end 128. The lateral opening 144 has the width W at the termination 154 of the guide and advancement structure 152. The back wall portion 138 extending between the threaded side walls 140 and 142 has an outer substantially planar and smooth surface finish.

In the intermediate portion 134 of the end guide tool 109, the substantially cylindrical side walls 140 and 142 include an outer radially extending bevel 156 transitioning into substantially cylindrical side walls 160 and 162 integral with the walls 140 and 142, respectively. The walls 160 and 162 uniformly increase the thickness of the respective side walls 140 and 142, resulting in a substantially cylindrical cross-section of greater outer diameter than a diameter created by an outer surface of the side walls 140 and 142 extending from the top 128 to the bevel 156. The walls 160 and 162 are configured with co-planar front facets 164 and 166, respectively, providing for alignment and mating with other tools, if desired.

Near the end or bottom 129 of each end guide tool 109, disposed on inner surfaces 168 and 170 of the side walls 160 and 162 respectively, is a radially inwardly extending, implant engaging, attachment structure, generally 172, illustrated in FIGS. 7-9 and described herein with respect to the identical structure 172 on the intermediate guide tool 110. Unless specifically stated otherwise, the intermediate guide tool 110 includes structure and features that can be utilized in similar fashion to what is described herein with respect to the end guide tool 109, and visa-versa.

The flat back wall portion 138 disposed primarily in the upper handle portion 132 terminates at an area 176 below and spaced from the guide and advancement structure 152 in the intermediate portion 134. Also at the area 176, the flat wall 138 forms a substantially circular aperture 178 communicating with a narrow elongate slot 180 that extends from the aperture 178 to a rod abutment opening 182 disposed near the base or bottom 129. The slot 180 has a side-to-side width that is substantially smaller than a diameter of the rod 3. The aperture 178, the narrow slot 180 and the opening 182 all communicate with the channel 126. The opening 182 further communicates with a base opening 184 that also communicates with the channel 126 and an exterior of the base 129. The aperture 178, slot 180 rod abutment opening 182 and base opening 184, along with the channel opening 144 disposed opposite thereto, all cooperate to allow for a spreading or splaying of the side walls 160 and 162 to provide a snap-on, snap-off cooperation between the implant engagement structure 172 and apertures 44 of the bone screw 1, as will be described more fully below.

Also in the vicinity or area 176 of the aperture 178, specifically, near where the aperture 178 communicates with the slot 180, the cylindrical side walls 140 and 142 each extend radially about a lower portion of the aperture 178 and towards one another, separated by the narrow slot 180. Similarly, the thicker side walls 160 and 162 disposed below the bevel 156 also are separated by the narrow slot 180.

Figure 34:
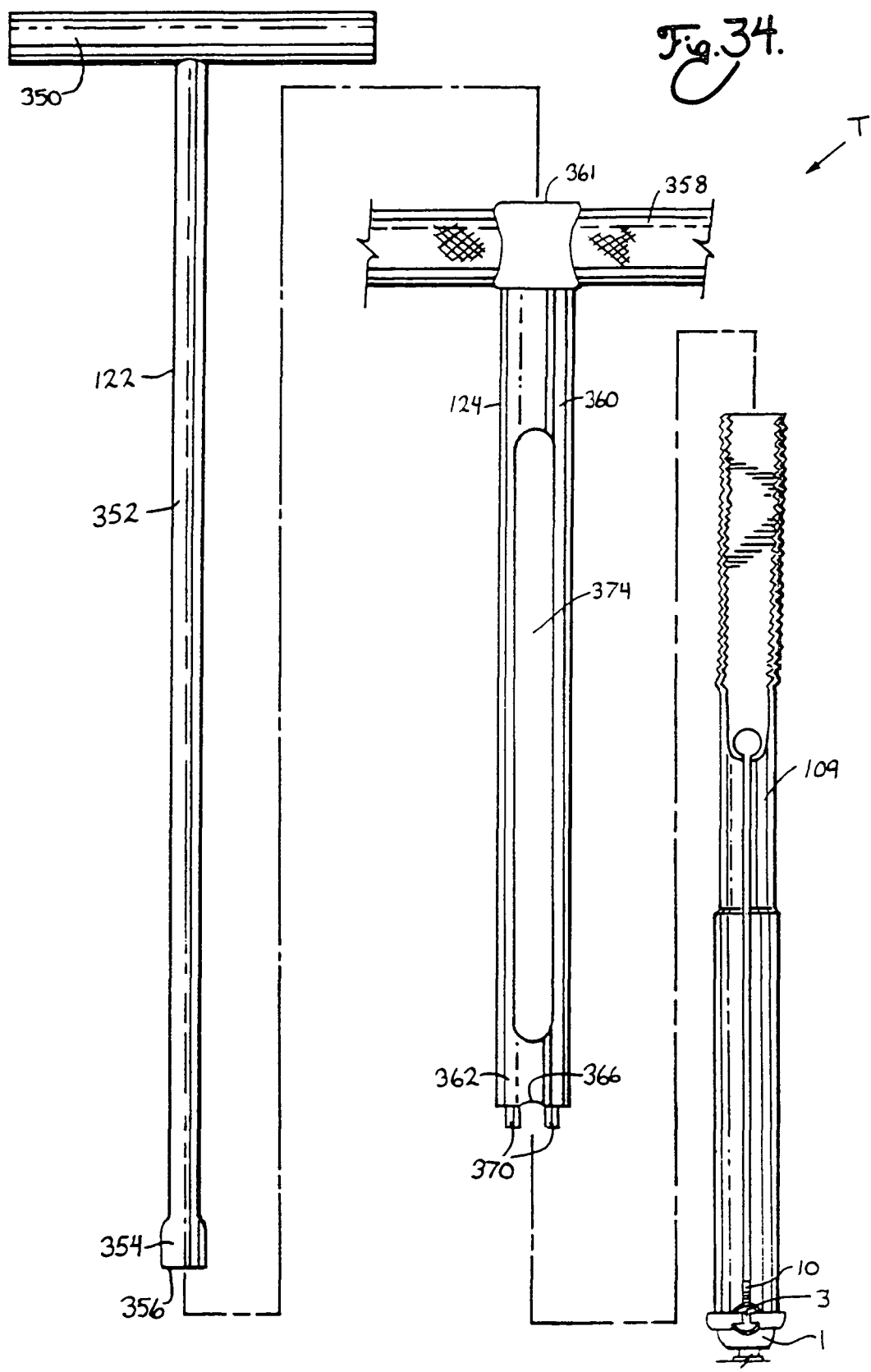
FIG. 34 is a reduced, partial elevational and exploded view of an assembly according to the invention, including a torquing tool, the anti-torque tool of FIG. 33 and the end guide tool of FIG. 3, further shown with a rod, bone screw and implant fastener.

Curved surfaces 188 and 190 at lower ends of the wall portions 160 and 162, respectively, define the opening 182 and are sized and shaped to fit about a portion of the cylindrical surface 66 of the rod 3. Disposed near the openings 182 and 184, and partially defining the bottom 129 is a rigid, laterally extending rod holding structure, generally 192, configured so that an end 193 of the rod 3 can extend beyond the bone screws 1 while abutting and being held in place by the holding structure 192, keeping the rod 3 in a desired position and under control. The rod holding structure 192 is generally disposed opposite the channel opening 144 and includes spaced arms 194 and 196 disposed on wall portions 160 and 162, respectively, sized and shaped to extend or wrap about the end 193 of the rod 3, as illustrated in FIGS. 34 and 37, with the rod end 193 abutting against the arms 194 and 196, and also extending outwardly beyond the surfaces 188 and 190. In addition to extending laterally opposite the channel opening 144, outside surfaces of the arms 194 and 196 extend radially outwardly at the walls 160 and 162, forming a ledge 198 that provides a stop for the rod pusher 114 and a seat for the anti-torque tool 124, as described more fully below. The arms 194 and 196 maintain the rod 3 at a desired location with respect to the bone screw 1, as well as controlling the lateral movement of the rod with respect to the intermediate tools 110, the other end tool 109, and respective cooperating bone screws 1.

Each of the intermediate guide tools 110, specifically illustrated in FIGS. 4 to 6, have a somewhat similar overall shape when compared to the end guide tools 109 in that both are preferably of the same axial length and width and also have much structure in common, with differences noted herein. With respect to inner profile, the guide tool 110 forms a channel 200 with an elongate lateral opening 202 of various widths, configured to receive, contain and allow translational movement along the channel 200, or rotational relative movement of certain tools, as described more fully below. The channel 200 extends from a top 204 to a bottom 205 of the guide tool 110, parallel to a central axis of rotation E thereof. The channel 200 is sized to accommodate elongate tools and bone screw components, such as the fastener or closure top 10.

Each intermediate guide tool 110 has an overall elongate body with an upper handle portion 206, an intermediate portion 208 and a lower implant engaging portion 210 which includes the structure 172 with opposed implant engaging members for securing one of the implants therebetween. In the upper portion 206, the tool 210 is generally C-shaped in cross-section. Each intermediate guide tool 110 upper or handle portion 106 has a substantially flat back wall 212 joining a pair of substantially cylindrically shaped side walls 214 and 216 separated by the axially extending channel opening 202. Similar to the opening 144 of the end guide tool 109, the opening 202 has a side-to-side width W near the top 204 that widens to the side-to-side width of W' in a mid-section of the handle portion 206, substantially narrows to the side-to-side width of W" and then widens again to the width W at a lower section of the upper handle portion 206.

Disposed on either side of the opening 202 at the width W" are co-planar surfaces 218 and 220 that are parallel with the back wall 212. It is foreseen that the surfaces 218 and 220, as well as the back or rear wall 212 may provide alignment surfaces when the intermediate guide tool 110 is utilized with other tools, such as certain drivers and rod pushers that also have flat cooperating surfaces. Below the surfaces 218 and 220, the side-to-side opening width W of the lateral opening 202 is substantially constant through the intermediate portion 208 and lower portion 210.

The upper or handle portion 206 also includes an outer helically wound discontinuous guide and advancement structure 222 disposed on outer sides of both of the substantially cylindrically shaped side walls 214 and 216, which may include conventional helically wound V-threads, helically wound square threads, buttress threads or other guide and advancement structure to cooperate with equivalent or mateable structure within the rod pusher 114 and the driver 112 as described more fully below. The guide and advancement structure 222 extends from near the intermediate portion 208 where the opening 202 has the width W" to the top 204. An outer surface of the rear or back wall 212 extending between the threaded side walls 214 and 216 is substantially planar and smooth.

The back wall 212 terminates at the intermediate portion 208, specifically at a location 224 where a lateral opening 226 begins and then extends from the location 224 to the bottom 205 of the tool 110. The opening 226 is open at the bottom 205, disposed opposite the opening 202, communicates with the channel 200, and also has the side-to-side width W. Thus, the openings 202 and 226 form a through-slot, dividing the side walls 214 and 216 into legs or prongs 228 and 230, respectively. The legs 228 and 230 have outer surfaces that are substantially cylindrical.

In the intermediate portion 208 of the guide tool 110, the legs 228 and 230 include an outer radially extending bevel 232 transitioning into substantially cylindrical side legs 234 and 236 integral with the legs 228 and 230, respectively. The legs 234 and 236 uniformly increase the thickness of the respective legs 228 and 230, resulting in a substantially cylindrical cross-section of greater outer diameter than a diameter created by an outer surface of the side walls 214 and 216, or the legs 228 and 230. At the base 205, both the legs 234 and 236 taper slightly radially inwardly, forming a bevel 237. The legs 234 and 236 also are configured with co-planar front facets 238 and 240, respectively, and rear facets 242 and 244, respectively, providing for alignment and mating with other tools, if desired.

With reference to FIGS. 7-9, at the lower portion 210, along inner surfaces 246 and 248 of the legs 234 and 236, respectively, is disposed the implant engaging structure, generally 172. The implant engaging structure 172 includes diametrically opposed projections or pins 250 and 252, both extending radially inwardly from the surfaces 246 and 248, respectively. The pins 250 and 252 are substantially configured the same, both being substantially rounded, radially inward projecting nodules, each having a lip 254 projecting upwardly and away from the bottom 205. Each lip 254 partially defines a groove 256 for receiving the bone screw 1. The groove 256 is further defined by a base surface 258 and a recessed wall 260. An upper wall 262 that is substantially parallel to the base surface 258 spans between the recessed wall 260 and the inner surface 246 or the inner surface 248.

Figure 14:
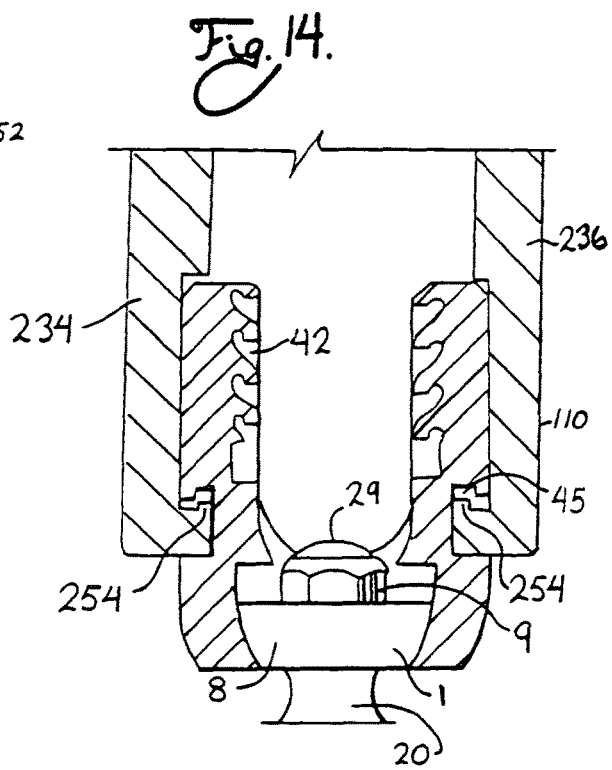
FIG. 14 is an enlarged cross-sectional view similar to FIG. 13 showing an intermediate stage of the snap-on attachment of the intermediate tool to the head.
Figure 15:
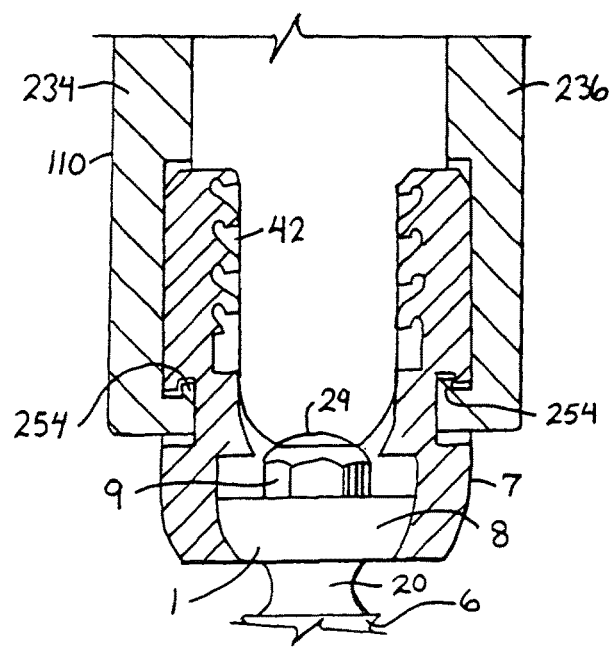
FIG. 15 is an enlarged cross-sectional view similar to FIG. 14, showing a final stage of the snap-on attachment of the intermediate tool to the head.

With reference to FIGS. 13-15, the pins 250 and 252 are configured to mate with the opposed apertures 44 of the bone screw 1 with the lip 254 extending into the inner recess 45, when the guide tool 110 is fully installed on the bone screw head 7 as shown in FIG. 15 and described more fully below. While a preferred embodiment of the invention has pins 250 and 252 of the implant engaging structure 172 on the guide tools 109 and 110, and apertures 44 and 45 on the bone screw heads 7, it is foreseen that these elements could be reversed in total or part in accordance with the invention or that other suitable attachment structure could be used.

With reference to FIGS. 16-18, the driver 112 of the tool set T of the invention includes a handle 270, a guide tool fastener or nut 272, and an elongate cylindrical stem or shaft 274, tapering to an integral lower cylindrical portion 275 having an inner surface bone screw engaging, socket structure 276. The socket 276 is configured to mate with the upper part of the nut 9 attached to the bone screw shank 6. The shaft 274 with attached socket 276 is receivable in and passes through the interior of the guide tools 109 and 110, such as the channel 200 of the guide tool 110. The lower portion 275 has a slightly smaller diameter than a diameter of the remainder of the shaft 274, this smaller diameter provides for adequate clearance of the portion 274 from the bone screw guide and advancement structure 42 when the shaft 274 is installed within the interior of the respective guide tools 109 and 110 and between the bone screw arms 34 and 35. The stem or shaft 274 is rigidly attached to the handle 270 and coaxial therewith. Both the handle 270 and the guide tool fastener 272 include outer grooves 278 and 279 respectively, about outer cylindrical surfaces thereof to aid in gripping and rotating the respective components.

The guide tool fastener 272 is a substantially hollow cylinder disposed in coaxial relationship with the handle 270 and the shaft 274. The fastener 272 has a threaded inner cylindrical surface 282 disposed at a lower portion 283 thereof, the threaded surface 282 configured to mate with the guide and advancement structure 152 of the end guide tool 109 or the guide and advancement structure 222 of the intermediate guide tool 110.

The driver 12 further includes a lateral pin 286 projecting radially outwardly from a cylindrical surface 288 adjacent the handle 270. In the embodiment shown, the cylindrical surface 288 is integral with the handle 270 and fixedly attached to the shaft 274. The pin 286 is disposed within an annular recess 290 defined by the cylindrical surface 288, and surfaces of the fastener 272, including an upper seating surface 292, a lower seating surface 294 and an inner cylindrical surface 296. The pin 286 disposed in the recess 290 allows for both rotational and axial or vertical translational movements of the fastener 272 with respect to the handle 270 and the shaft 274. Thus, as shown in FIG. 18, the fastener 272 is freely rotatable about an axis F independent of the shaft 274. Furthermore, the fastener is slidable along the axis F, with FIG. 16 showing a first or unattached position with the fastener 272 in contact with the handle 270 and FIGS. 17 and 18 showing a second, engagement position, with the fastener 272 spaced from the handle 270, with the pin 286 abutting the upper seating surface 292 prohibiting further downward or vertical (axial) translational movement of the fastener 272 with respect to the shaft 274.

The driver 112 is sized and shaped such that, when the fastener or nut 272 is slid into the second position shown in FIGS. 17 and 18 and the fastener threaded surface 282 is mated with the guide and advancement structure 152 of the end guide tool 109 or the guide and advancement structure 222 of the intermediate guide tool 110 as shown in FIG. 19, by rotating the fastener 272 in a clockwise direction, the socket 276 descends upon and engages with the outer surface of the nut 9 as shown in FIGS. 20 and 21. When the socket 276 abuts against the retaining ring top surface 58, and the fastener nut 272 is fully mated to the guide tool 109 or 110, relative axial movement between the driver 112 and the guide tool 109 or 110 is prevented. However, the driver handle 270 and attached stem 274 are freely rotatable with respect to the fastener 272 about the Axis F, and the bone screw nut 9 and attached bone screw shank 6 also are freely rotatable with respect to the bone screw head 7 and attached guide tool 109 or 110, about the Axis A, which is coaxial with the Axis F. Thus, the driver 112 and engaged bone screw shank 6 may be rotated and the shank body 15 driven into a vertebra 2 as shown in FIG. 22 and discussed more fully below, while the bone screw head 7 is controlled and held in a stable, non-rotating position by the non-rotating guide tool 109 or 110. After the bone screw shank body 15 is driven into bone, the driver 112 may be easily removed from the guide tool 109 or 110 by rotating the fastener 272 in a counter-clockwise direction and lifting the driver 112 away and out of the guide tool 109 or 110.

Figure 23:
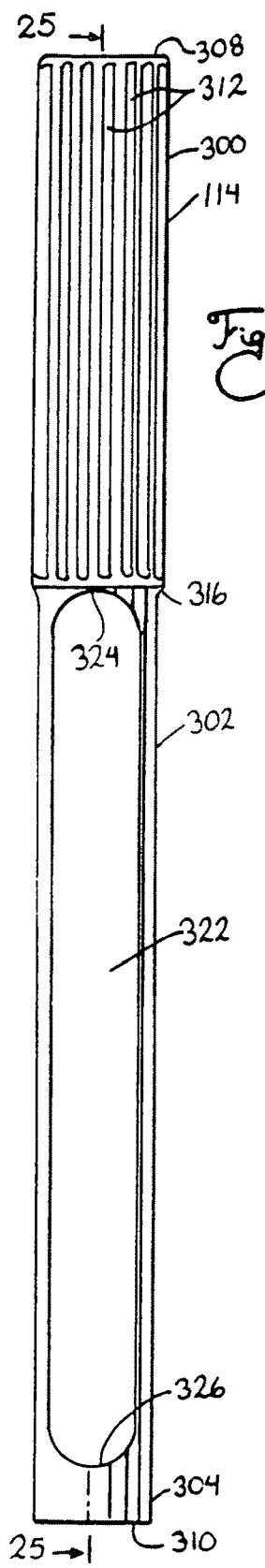
FIG. 23 is a front elevational view of a rod pusher according to the invention.
Figure 24:
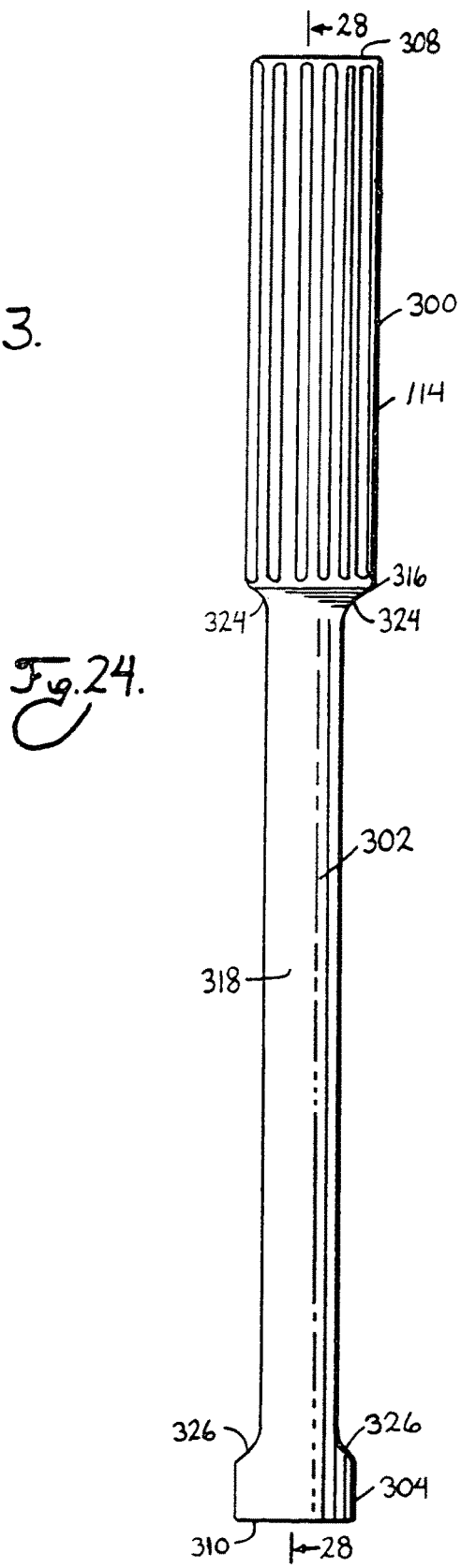
FIG. 24 is a side elevational view of the rod pusher of FIG. 23.
Figure 25:
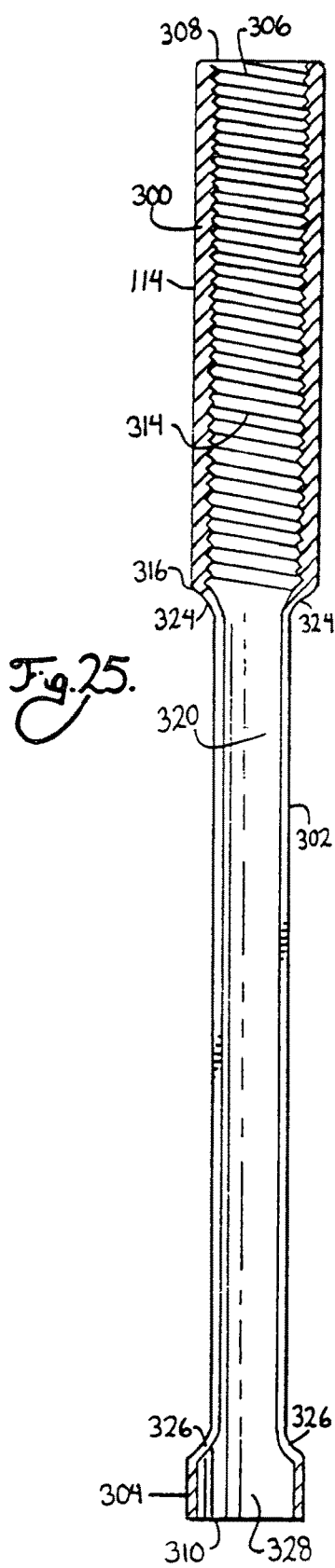
FIG. 25 is a cross-sectional view taken along the line 25-25 of FIG. 23.

The rod pusher 114 of the tool set T is illustrated in FIGS. 23-25 and 27-31. With particular reference to FIGS. 23-25, the rod pusher 114 is elongate and substantially cylindrical, having an upper handle portion 300, a sleeve 302 and a lower rod-engaging portion 304. An open inner channel 306 extends from a top 308 to a bottom 310 of the rod pusher 114. The rod pusher 114 is configured to closely receive a guide tool 109 or 110 within the channel 306 as illustrated in FIGS. 27-31.

The upper handle portion 300 has a cylindrical outer surface that has outer grooves 312 to aid in gripping and rotating the rod pusher 114. The upper handle portion also has a substantially cylindrical, threaded, inner surface 314, configured to mate with either the guide and advancement structure 152 of the end guide tool 109 or the guide and advancement structure 222 of the intermediate guide tool 110. The threaded surface 314 extends from the top 308 to a location 316 where the handle portion 300 integrally connects with the sleeve 302.

The sleeve 302 includes an outer cylindrical surface 318 and an inner cylindrical surface 320, substantially removed by an elongate through-slot 322, partially defined by a U-shaped top 324 and a U-shaped bottom 326. The U-shaped bottom 326 is spaced from the rod pusher bottom 310. The lower rod-engaging portion 304 is substantially cylindrical, integral with the sleeve 302 and extends from the bottom 310 to the U-shaped bottom 326 of the through-slot 322. A cylindrical inner surface 328 at the rod-engaging portion 304 is integral and coaxial with the sleeve inner surface 320, which in turn is integral and coaxial with the inner threaded surface 314. The inner surfaces 320 and 328 are configured to closely receive and contain the guide tool 109 at the thick side walls 160 and 162 and the guide tool 110 at the legs 234 and 236. The rod pusher 114 is configured to be received about the guide tool 109 or 110, with the substantially circular bottom 310 pressing against the outer cylindrical surface 66 of the rod 3 at either side of the guide tool 109 or 110, as shown, for example in FIG. 29. Clockwise rotation of the rod pusher 114 about the guide tool 109 or 110 causes the threaded surface 314 to mate with either the guide and advancement structure 152 or the guide and advancement structure 222, and continued rotation translates the rod pusher bottom surface 310 downwardly, toward the bone screw 1 as shown in both FIGS. 29 and 30. The inner threaded surface 314 is of a length that provides an equivalent translation distance of the rod pusher bottom 310, so that the bottom is translatable along the guide tool 109 or 110 to a location wherein the rod 3 is fully seated within the bone screw 1 as illustrated in FIG. 31.

With reference to FIGS. 27-29 and 31, a three-component assembly of the tool set of the invention includes a guide tool 109 or 110, a rod pusher 114 and a manipulation tool 118. The manipulation tool 118 with an attached fastener, such as the closure top 10 may also be utilized to press against the rod 3, alone or in cooperation with a rod pusher 114 as shown in FIG. 29 and described more fully below. Also as shown in FIG. 29, it may be desirable to utilize only one rod pusher 114 for a tool set T. In certain procedures, more rod pushers 114 may be desired.

The manipulation tool 118 includes a handle 330, fixedly attached to or integral with an elongate stem 332 having a lower fastener engagement end portion 334. Similar to the other tools in the tool set T, the handle 330 preferably includes outer grooves 336 to aid in gripping and rotating the tool 118. The handle 330 and stem 332 are configured to be received by the guide tool 109 or the guide tool 110 at the channels 126 and 200, respectively, with the handle 330 being closely received thereby so as to provide axial alignment between the tool 118 and the guide tool 109 or 110, providing efficient guidance and control of the fastener 10 into the bone screw 1. As illustrated in FIG. 28, the manipulation tool 118 is configured to have a length to allow a substantial portion of the handle 330 disposed above the guide tool 109 or 110 during attachment of the fastener 10 to the bone screw 1 for ease in handling and manipulation of the fastener 10 within the channel 126 or 200 and between the bone screw arms 34 and 35.

With special reference to FIG. 31, the fastener engagement end portion 334 includes a projection 340 extending from a bottom 342 of the stem 332 to a tapered end portion 344 receivable into the central bore 77 of the closure top break-off head 68. The projection 340 and tapered end portion 344 have a maximum diameter that is smaller than a maximum diameter or width of the stem 334. Also extending from the bottom 342 of the stem 332 are opposed nubs 356 that are receivable in the pass-through slot 78 of the break-off head 68 at either side of the projection 340. When inserted in the break-off head 68, the projection 340 and nubs 356 cooperate to securely attach the closure top 10 to the manipulation tool 118 during insertion of the closure top 10 into the guide tool 109 or 110 and the bone screw 1, but also be easily detachable from the bone screw 1 by pulling the tool 118 upwardly axially and out of the guide tool 109 or 110 once the closure top 10 is rotated and secured between the arms 34 and 35 of the bone screw head 7.

Once the closure top 10 is seated in the bone screw 1, the torquing tool 122 and cooperating anti-torque tool 124 are utilized to tighten the closure top 10 in the screw head 7 and remove the break-off head 68. The torquing tool 122 and anti-torque tool 124 are illustrated in FIGS. 32-36. The torquing tool 122 shown in FIG. 34, includes an upper handle portion 350 disposed perpendicular to an elongate stem 352 that is integral to a lower closure top engagement portion 354 having an inner surface defining a socket 356 configured for mating with and rotating the faceted surface 75 of the closure top break-off head 68. The elongate stem 352 is configured to be received in the guide tool 109 or 110, with the handle 350 at a desired height there-above to allow for sufficient mechanical advantage and ease in rotating the stem 352 to set the closure top 10, so it is snug against the rod 3, and thereafter break away and remove the break-off head 68 in the manner shown in FIGS. 35 and 36.

With particular reference to FIGS. 32 and 33, the anti-torque tool 124 includes an elongate handle 358 fixed to a tubular hollow shaft 360 that is sized and shaped to be slidably received over the guide tool 109 or 110. The handle 358 is disposed perpendicular to the shaft 360 and has an opening 361 through which the torquing tool 122 passes in the manner suggested by FIG. 34. The shaft 360 has a lower end portion 362 that has a pair of diametrically spaced, curved bridges 364 and 366. Both of the bridges 364 and 366 are sized and shaped to fit over the surface 66 of the rod 3 as illustrated in FIGS. 35 and 36. The curved bridge 364 further includes extensions 370 that provide additional coverage about the surface 66 of the rod 3 and are particularly useful for holding the rod 3 in place when used with the end tool 109. A bottom surface 372 adjacent the bridge 366 seats on the ledge 198 of the rod holding structure 192 of the end guide tool 109, while the extensions 370 disposed opposite thereof, extend downwardly on either side of the rod 3 and are flush with the front facets 164 and 166 of the guide tool 109. Disposed between the handle 358 and the lower end portion 362 is an elongate through-slot 374 with U-shaped ends, similar to the slot 322 of the rod pusher 114. When in place, as illustrated in FIGS. 35 and 36, the anti-torque tool 124 allows a surgeon to counter the torque applied by the torquing tool 122, when applying torque to and breaking away the break-off head 68.

In use, the previously described tools are utilized to attach one or more rods 3 to the human spinal column 4. The procedure is begun by selection of a bone screw 1 in accordance with the size of the patient's vertebra 2 and the requirements of the spinal support needed. Bone screws having a rotatable or polyaxial head are preferred but not required for the procedure, as such allow relatively easy adjustment of the rod 3 in the guide tools 109 and 110 during placement and for movement of the tools 109 and 110, as described below. The bone screw may also be cannulated so as to be receivable over and guided by a guide pin, if desired.

A relatively small incision, such as an incision 380 in the skin 130 is made for each bone screw 1 to be used. Preferably, the incisions are sized so as to snugly receive the tools of the invention. The incisions 380 are stretched into a round shape with a circumference slightly larger than the guide tool 109 and 110. The skin 20 is relatively flexible and allows the surgeon to move the incision 380 around relative to the spine 4 to manipulate the various tools and implants, as required. In some cases, two screws can be inserted through the same incision.

With reference to FIG. 22, guide bores may be drilled in the vertebra 2 prior to implantation of bone screws 1 therein. This may be accomplished with non-invasive imaging techniques, which procedures are known and established. The guide bores are then preferably enlarged and shaped to correspond with the thread-type of the bone screw 1 to be used.

Before implanting the bone screw 1 in the vertebra 2, the bone screw 1 is preferably joined to an associated guide tool 109 or 110 and an associated driver 112. It is possible, but typically not desirable, to join a guide tool 109 or 110 to the bone screw 1 after the installation of the bone screw 1 to the vertebra 2. The implant engaging structure 172 disposed on both the end guide tool 109 and the intermediate guide tool 110 is joined to a bone screw 1 by first manually spreading the walls 160 and 162 apart; or the legs 234 and 236 apart; and inserting the guide tool 109 or 110 onto the bone screw head 7 as illustrated in FIG. 13 with respect to an intermediate guide tool 110. The inwardly projecting pins 250 and 252 are generally aligned with the apertures 44 and the tool is slid downwardly along the head 7 surface until the pins 250 and 252 snap into the apertures 44 as shown in FIG. 14. With reference to FIG. 15, the guide tool 110 is then pulled upwardly and away from the bone screw 7, causing the lips 254 to enter the recesses 45. Engagement between the lips 254 and the structure defining the recesses 45 result in a firm attachment that also resists any attempt to spread or splay the arms 234 and 236.

The snap-on procedure described herein with respect to the intermediate tool 110 is also followed with respect to the end guide tool 109 attachment structure 172. Splaying of the walls 160 and 162 is possible because the aperture 178, slot 180 and openings 182 and 184, cooperate with the opposite channel opening 144, resulting in adequate flexibility for spreading or extending the opposing walls 160 and 162 about the head 7 of the bone screw 1 as shown in FIG. 13. If desired, a tool may be inserted in the aperture 178 and then into the slot 180 to aid in splaying the walls 160 and 162.

After the bone screws 1 have been attached to the guide tools 109 and 110, a driver 112 is then attached to the guide tool 109 or 110 for implanting the attached bone screw 1 in a vertebra 2. With reference to FIGS. 19-21, the driver 112 is installed by inserting the socket end 276 into the channel 126 or 200 of the top 128 or 204, respectively of the respective guide tool 109 or 110. The driver is then advanced down the channel 126 or 200 until the threaded inner surface 282 of the driver fastener 272 contacts the guide and advancement structure 152 or 222 of the guide tool 109 or 110, respectively. Then the fastener 272 is rotated in a clockwise direction (as viewed from the top of the handle 270) until there is resistance to rotation caused by the socket 272 surrounding the nut 9 and abutting against the top 58 of the retaining ring 8 of the bone screw 1 as illustrated in FIG. 21. A slight rotation or jiggling of the bone screw shank 6 may be required for the hex socket 276 of the driver 112 to become positioned in operational engagement with the hex-shaped facets 13 of the nut 9. Hand-tightening of the fastener 272 after the socket 272 is positioned about the nut 9, ensuring that the lips 254 of the implant engaging structure 172 are abutting against the bone screw head 7 at the inner recesses 45, thus securely mating the bone screw 1 to the guide tool 109 or 110 during the bone screw implantation process. The assembly shown in FIG. 19 that includes a bone screw 1, an intermediate guide tool 110 and a driver 112 is now ready for bone screw installation into the vertebra 2. FIG. 22 illustrates a driver similarly installed in an end guide tool 109.

A series of bone screws 1 are installed in each vertebra 2 to be attached to the rod 3 by inserting the bone screw, guide tool and attached driver assemblies through the skin incision 380 as shown in FIG. 22. The screw 1 is then rotated and driven into a tapped bore with the surgeon holding the guide tool 109 or 110 stationary and rotating the driver 112 by the handle 270, until the shank body 15 is disposed at a desired depth in the tapped bore of the respective vertebra 2.

After a specific bone screw 1 is installed, the driver 112 is removed from either the guide tool 109 or 110 by rotating the fastener 272 in a counter-clockwise direction and pulling the driver 112 out of the assembly and away from the incision 380 using the handle 270.

For each implanted bone screw 1, an associated guide tool 109 or 110 extends through the skin 130, as illustrated in FIG. 29. An end guide tool 109 is located at each end of the series of bone screws 1 with the channel opening 144 facing toward the intermediate guide tools 110 disposed between the end guide tools 109. The intermediate guide tools 110 are implanted in an alignment such that the lateral openings 202 and 226 align with the channel openings 144 of the end guide tools 109.

In order to install a rod 3 in two or more bone screws 1, it may not be necessary to equip each guide tool 109 or 110 with a rod pusher 114. For example, with reference to FIG. 29, for a particular procedure, it may be desirable to utilize only one rod pusher 114 with a tool set T according to the invention. Some pushing of the rod may be accomplished by just extending a rod or tool down the central channel of the guide tools 109 and 110 when mechanical advantage is not required to move the rod 3. As required by the surgeon, one or more rod pushers 114 may be added or removed at any time during the course of the rod pushing or reducing procedure.

With reference to FIG. 29, the rod end 193 has been inserted diagonally through one of the end skin incisions 380 with the adjacent end guide tool 109 pushed to the side, so that one of the rod ends 193 first passes through the lateral openings 202 and 226 in the intermediate guide tools 110 and then into the lateral opening 144 of the channel 126 of one of the guide tools 109. Back muscle tissue separates easily here to allow the upper insertion of the rod 3 and can be further separated by finger separation or cutting through one of the incisions 380, if required.

After initial insertion, the remaining opposed end 193 of the rod 3 is positioned in the channel 126 of the end guide tool 109 that is located next to the insertion point of the rod 3. Manipulation of the rod 3 in the channels 126 and 200 may be aided by a manipulation tool 118 and attached fastener 10 as illustrated in FIG. 29 and also by the guide tools 109 and 110 themselves which may be moved toward or away from each other by the surgeon. For example, when the rod 3 is spaced above the bone screws 1, the guide tools 109 can be manipulated to be spaced farther apart to receive the rod 3 therebetween. As the rod 3 nears the bone screws 1, the rod ends 193 are slid through the rod abutment opening 182 and into the rod holding structure 192 to allow the rod 3 to extend slightly beyond the bodies of the guide tools 109. The rod holding structures 192 allow the rod 3 to be controlled and positioned outwardly of the end bone screws 1, approximately an equal amount on each side.

Also with reference to FIG. 29, once the rod 3 is positioned in the guide tools 109 and 110, the rod pusher 114 may be utilized to push the rod 3 toward the bone screw 1, normally when mechanical advantage is needed to seat the rod 3 in the bone screws 1. In the illustrated embodiment, this is accomplished by inserting the rod pusher 114 over an intermediate guide tool 110 and then rotating the rod pusher 114 in a clockwise direction (as viewed from above the skin 130), mating the threaded inner surface 314 with the guide and advancement structure 222, thereby translating the sleeve 302 in a downward direction toward the bone screw 1, with the rod pusher bottom 310 abutting and pushing against the rod 3.

As shown in FIG. 29, it may also be desirable to simultaneously or thereafter push the rod 3 toward the screw 1 of one or more guide tools 109 and 110 utilizing the manipulation tool 118 pushing against a closure top 10 that in turn pushes against the rod 3. In particular, a closure top 10 is attached to the manipulation tool 118 with the projection 346 of the tool inserted into the central bore 77 of the closure top 10 and the nubs 346 inserted into the grooves 78. Then the closure top 10 is inserted into the channel 126 or 200 of the guide tool 109 or 110, respectively, by top entry or side entry through the respective lateral channel opening 144 or 202. If the rod pusher 114 is being utilized on the guide tool 109 or 110, then entry though the respective top 128 or 204 would be necessary. If desired, the closure top 10 may first be inserted in the guide tool 109 or 110 by top or side entry and then the manipulation tool 118 may be inserted into the top and moved through the channel 126 or 200 until the fastener engagement end 334 mates with the cooperating break-off head 68 of the closure top 10. The closure top 10 is then pushed under manual control of the surgeon holding the handle 330 of the manipulation tool 118.

With reference to FIG. 31, when the closure top 10 guide and advancement structure 71 abuts against the guide and advancement structure 42 on the inner surface of the head 7 of the bone screw 1, the manipulation tool 118 is then rotated, mating the closure top 10 with the bone screw 1 and driving the closure top 10 downward against the rod 3 to urge the rod 3 into final placement in the bone screw U-shaped channel 38 so as to snug against and frictionally lock the shank 6 in position relative to the bone screw head 7. As shown in FIG. 31, the manipulation tool 118 is then pulled axially upwardly away from the bone screw 1 and out of the incision 380.

Once all of the closure tops 10 are in a final seated position in respective bone screws 1 and the surgeon is satisfied with the position of all of the elements, any and all rod pushers 114 are removed by rotating the rod pusher 114 counter-clockwise followed by sliding the sleeve 302 off of the guide tool 109 or 110 and out of the incision 380.

The anti-torque tool 124 is mounted over each guide tool 109 and 110, utilizing the respective guide tool as a guide for re-entry through the incision 380. With respect to the end tool 109, the anti-torque tool 124 is slid along the tool 109 until the bridges 364 and 366 straddle the rod 3, with the bridge 366 disposed over the rod holding structure 192 at the back of the tool 109 and the extensions 370 straddling the rod adjacent the lateral opening 144 at the front thereof, the bridges 364 and 366 cooperating to prevent rotation of the tool 124. The bottom surface 372 of the anti-torque tool 124 also seats on the ledge 198 of the rod holding structure 192, providing increased stability. When the anti-torque tool is placed on an intermediate guide tool 110, the bridges 364 and 366 are simply aligned with and placed over the rod 3, without reference to a front or back of the tool 110.

With reference to FIGS. 34-36, the torquing tool 122 is then inserted into the guide tool 109 or 110 and cooperating anti-torque tool 124 and engaged with the break-off head 68. By cooperative use of the tools 122 and 124, a preselected torque is manually applied to the break-off head 68 which breaks from the closure top 10 as illustrated in FIGS. 35 and 36 and is thereafter removed, followed by removal of the anti-torque tool 300.

Thereafter, each of the guide tools 109 and 110 are removed from the attached bone screws 1. With respect to the end guide tool 109, downward force is first placed on the guide tool 109 by the surgeon to move the lips 254 of the guide tool implant engaging structure 172 out of the inner recesses 45 of the bone screw head 7. Then a prying tool may be inserted in the aperture 178 and then along the slot 180 to spread the side walls 160 and 162, while pulling up on the guide tool 109 to allow the guide tool to slide upwardly along the bone screw head 7 (as illustrated in reverse by FIGS. 15, 14 and 13).

Similarly, with respect to the intermediate guide tools 110, downward force is first placed on the guide tool 110 by the surgeon to move the lips 254 of the guide tool implant engaging structure 172 out of the inner recesses 45 of the bone screw head 7. Then a prying tool may be inserted between the legs 228 and 230 to spread the lower legs 234 and 236, while pulling up on the guide tool 110 to allow the guide tool to slide upwardly along the bone screw head 7 (as illustrated in reverse by FIGS. 15, 14 and 13).

The guide tool 109 or 110 is then pulled axially upwardly away from the bone screw 1, and then out of the incision 350. Finally, the incision is closed.

It is to be understood that while certain forms of the present invention have been illustrated and described herein, it is not to be limited to the specific forms or arrangement of parts described and shown.

What is claimed is:

1. A tool set for implanting a rod in a patient using at least one spinal implant, the tool set comprising:
    a guide tool comprising:
    an elongate body having a longitudinal axis, an outer surface and a channel with a first channel opening extending laterally through the outer surface and along the longitudinal axis for a length of the guide tool, the channel and the first channel opening sized and shaped to receive the rod; and
    a spinal implant engaging structure near a bottom of the elongate body comprising a first projection and a second projection opposed to the first projection, the first projection projecting into the channel, and an upwardly projecting lip projecting upward from the first projection, wherein the first projection and the upwardly projecting lip are sized and shaped to be received together completely in an inwardly projecting aperture of an engagement feature of the spinal implant at a first stage of engaging the at least one spinal implant, and wherein the upwardly projecting lip is sized and shaped to be received in an inner recess projecting upwardly from the inwardly projecting aperture of the engagement feature of the spinal implant at a second stage of engaging the at least one spinal implant.

2. The tool set of claim 1, wherein the guide tool is an end guide tool and the channel and channel opening are sized and shaped for side loading and receiving of an end of the rod.

3. The tool set of claim 2, wherein the end guide tool further includes a slot disposed opposite the channel opening, the slot and channel opening cooperating to allow manual flexing of the guide tool body to increase a distance between the first projection and the second projection during insertion of a spinal implant into the end guide tool.

4. The tool set of claim 1, wherein the guide tool is an intermediate guide tool, the elongate body comprises each of a first elongate leg and a second elongate leg and further defines a second channel opening opposite the first channel opening such that the elongate body defines an elongate through-slot sized and shaped for receiving the rod therethrough.

5. The tool set of claim 4, wherein the first projections are disposed on the first elongate leg and the second projection is disposed on the second elongate leg.

6. The tool set of claim 5, wherein the through-slot allows for manual flexing of at least one of the first elongate leg and the second elongate leg to increase a distance between the first projection and the second projection during insertion of a spinal implant into the end guide tool.

7. The tool set of claim 1, wherein the first projection and the second projection are inwardly biased.

8. The tool set of claim 1 further comprising a driving tool attachable to the guide tool, the driving tool receivable in the channel and operably attachable to the spinal implant for rotating and driving the spinal implant.

9. The tool set of claim 8 wherein the guide tool further comprises an outer guide and advancement structure and the driving tool comprises a fastener including an inner guide and advancement structure rotatingly mateable with the outer guide and advancement structure.

10. The tool set of claim 9, wherein the driving tool further comprises a stem and a driving structure disposed at a lower end of the stem, the driving structure for rotating and driving the spinal implant, and the fastener is freely rotatable with respect to the stem.

11. The tool set of claim 10 wherein the driving structure is an internal surface forming a socket for receiving an upper portion of the spinal implant.

12. The tool set of claim 1 further comprising a rod pusher attachable to the guide tool, the rod pusher comprising a sleeve and a driving end, the sleeve receivable over the elongate body and operably attachable to the elongate body such that rotational movement of the sleeve translates the driving end along the body.

13. The tool set of claim 12 wherein the guide tool comprises an outer guide and advancement structure and the rod pusher comprises an inner guide and advancement structure rotatingly mateable to the outer guide and advancement structure.

14. The tool set of claim 1 further comprising an elongate torquing tool having a handle and a stem receivable in the channel of the guide tool and attachable to an implant fastener.

15. The tool set of claim 1 further comprising an elongate anti-torque tool comprising a sleeve receivable over the elongate body of the guide tool, the sleeve sized and shaped to seat upon and abut against a rod at either side of the elongate body such that the sleeve precludes any rotational movement of the anti-torque tool relative to the guide tool.

16. A tool set for implanting a rod in a patient using at least one spinal implant, the tool set comprising:
    a guide tool comprising:
    an elongate body; and
    a spinal implant engaging structure near a bottom of the elongate body comprising a first projection and a second projection opposed to the first projection, and an upwardly projecting lip projecting upwardly from the first projection, wherein the first projection and the upwardly projecting lip are sized and shaped to be received together completely in an inwardly projecting aperture of an engagement feature of the spinal implant at a first stage of engaging the at least one spinal implant, and wherein the upwardly projecting lip is sized and shaped to be received in an inner recess projecting upwardly from the inwardly projecting aperture of the engagement feature of the spinal implant at a second stage of engaging the at least one spinal implant.

17. The tool set of claim 16, wherein the guide tool is an end guide tool and the elongate body defines a channel and a channel opening sized and shaped for side loading and receiving of an end of the rod.

18. The tool set of claim 16, wherein the guide tool is an intermediate guide tool and the elongate body defines a through-slot sized and shaped for receiving the rod therethrough.

19. The tool set of claim 16, wherein the first and second projection are inwardly biased.

20. A tool set for implanting a rod in a patient using at least one spinal implant, the spinal implant including engagement features having upwardly projecting inner recesses, the tool set comprising:

a first end guide tool;
a second end guide tool; and
at least one intermediate guide tool, each of the first end guide tool, the second end guide tool and the at least one intermediate guide tool comprising:
an elongate body; and
a spinal implant engaging structure near a bottom of the elongate body comprising a first projection and a second projection opposed to the first projection, and an upwardly projecting lip on the first projection, wherein the first projection and the upwardly projecting lip are sized and shaped to be received together in an inwardly projecting aperture of an engagement feature of the spinal implant at a first stage of engaging the at least one spinal implant, and wherein the upwardly projecting lip is sized and shaped to be received in an inner recess projecting upwardly from the inwardly projecting aperture of the engagement feature of the spinal implant at a second stage of engaging the at least one spinal implant.

\* \* \* \* \*